(12) United States Patent
Kanomata et al.

(10) Patent No.: US 8,915,261 B2
(45) Date of Patent: Dec. 23, 2014

(54) PRESSURE CONTROL APPARATUS FOR SUPERCRITICAL FLUID

(75) Inventors: Takeshi Kanomata, Hachioji (JP); Kazuharu Okubo, Hachioji (JP); Seiji Horioka, Hachioji (JP)

(73) Assignee: Jasco Corporation, Tokyo (JP)

( * ) Notice: Subject to any disclaimer, the term of this patent is extended or adjusted under 35 U.S.C. 154(b) by 497 days.

(21) Appl. No.: 12/912,957

(22) Filed: Oct. 27, 2010

(65) Prior Publication Data

US 2011/0094606 A1    Apr. 28, 2011

(30) Foreign Application Priority Data

Oct. 28, 2009   (JP) ................................ 2009-247535

(51) Int. Cl.
*G05D 16/20*  (2006.01)
*G01N 30/32*  (2006.01)
*B01D 15/40*  (2006.01)

(52) U.S. Cl.
CPC ............... *G01N 30/32* (2013.01); *B01D 15/40* (2013.01); *G05D 16/202* (2013.01); *G01N 2030/328* (2013.01)
USPC ................... 137/486; 137/487.5; 251/129.06; 251/285

(58) Field of Classification Search
USPC ............... 251/129.06, 285; 137/486, 487.5
See application file for complete search history.

(56) References Cited

U.S. PATENT DOCUMENTS

| | | | | |
|---|---|---|---|---|
| 4,884,720 A | * | 12/1989 | Whigham et al. | ............... 222/54 |
| 4,984,602 A | | 1/1991 | Saito et al. | |
| 5,224,510 A | | 7/1993 | Pericles | |
| 6,895,351 B2 | * | 5/2005 | Grumstrup et al. | ............. 702/98 |
| 7,117,886 B2 | * | 10/2006 | Kajitani et al. | ............. 137/487.5 |

FOREIGN PATENT DOCUMENTS

| | | |
|---|---|---|
| EP | 0438184 | 7/1991 |
| EP | 1785623 | 5/2007 |
| EP | 1909157 | 4/2008 |
| FR | 2587123 | 3/1987 |
| JP | 8-030989 | 3/1996 |
| WO | 9114941 | 10/1991 |

* cited by examiner

*Primary Examiner* — William McCalister
(74) *Attorney, Agent, or Firm* — Rankin, Hill & Clark LLP

(57) ABSTRACT

A pressure control apparatus for a supercritical fluid according to the present invention includes: a valve comprising; a valve chamber provided in a midway of a channel through which a supercritical fluid passes; and an electrically-operated valve element located in the valve chamber; a pressure detection member for detecting the pressure of the supercritical fluid in the channel on an upstream or downstream side of the valve chamber; an open/close control member for controlling the pressure detected by the pressure detection member to be a target pressure; and a valve-opening rate adjustment member for adjusting the valve-opening rate when the valve is opened based on the state of the supercritical fluid.

12 Claims, 21 Drawing Sheets

(a)

(b)

(c)

PRESSURE CONTROL APPARATUS FOR SUPERCRITICAL FLUID

RELATED APPLICATIONS

This application claims the priority of Japanese Patent Application No. 2009-247535 filed on Oct. 28, 2009, which are incorporated herein by reference.

FIELD OF THE INVENTION

The present invention relates to a pressure control apparatus for a supercritical fluid, and particularly to an improvement in a valve element control method used with the same.

BACKGROUND OF THE INVENTION

A supercritical fluid is widely used in chromatography or specific constituent fractionation because of its permeability to an object, high extractability in mild conditions, and other properties.

In particular, supercritical fluid chromatography is known to have a greater degree of freedom than liquid chromatography in terms of various liquid delivery conditions, such as the flow rate, pressure, temperature, modifier composition ratio.

However, a supercritical fluid has characteristics that are not seen in typical liquids in that a high pressure is required to maintain supercritical conditions and the density of the supercritical fluid greatly varies with pressure. When the density of a supercritical fluid as a mobile phase varies, the elution power of the fluid varies. Therefore, to obtain a satisfactory chromatogram, it is essential to reduce the variation in the density of the supercritical fluid and thus the pressure in a supercritical fluid system. To this end, a special pressure control apparatus is required.

For example, Japanese Patent Publication No. 8-30989 discloses a pressure control apparatus of related art preferably used with a supercritical fluid.

The pressure control apparatus disclosed in Japanese Patent Publication No. 8-30989 has a valve comprising a valve chamber provided in a midway of a channel through which a supercritical fluid flows and a valve element disposed in the valve chamber in such a way that the valve element can travels forward and backward. The valve is used to open and close the channel, through which the supercritical fluid flows, and a control circuit is used to control the pressure in the channel by adjusting the open/close cycle of the valve and the duty ratio thereof.

The apparatus of the related art can reduce the amount of fluid left in the valve chamber and prevent substances contained in the fluid from attaching to the inner wall of the valve chamber.

DISCLOSURE OF THE INVENTION

Problem to be Solved by the Invention

In a supercritical fluid system, since a small change in pressure greatly changes the density of the fluid due to the properties of a supercritical fluid, a slight variation in pressure produced when the valve is opened or closed in response to a pressure control operation affects measurement. To stabilize the pressure in the supercritical fluid system, it has therefore been believed that it is necessary to not only control the open/close cycle and the duty ratio thereof to achieve a target pressure of the system but also adjust the valve-opening rate based on the stroke of the valve element to suppress the variation in the pressure in the system due to the control operation. In particular, in measurement in which the pressure, flow rate, composition of the supercritical fluid, and other analysis conditions are changed with time and fine pressure control according to any change in the conditions is performed, it is necessary, whenever the pressure control is performed, to adjust the stroke to a value that minimizes the pressure variation due to the control operation.

In the related art, however, no consideration is made on valve-opening ratio adjustment based on the stroke, but the stroke of the valve element is simply adjusted manually before each measurement. In this case, in measurement in which the analysis conditions are changed as described above, it is practically impossible to adjust the stroke to an appropriate value in accordance with the change in the conditions. As a result, in the pressure control apparatus of the related art, the pressure variation produced when the valve element travels forward or backward may disadvantageously increase. Further, the manual adjustment requires significant time and effort and causes adjustment errors because the adjustment varies from person to person, and any change in mechanical components due to long-term use may change the way in which the adjustment is made.

Also, in the pressure control apparatus of the related art, any change in the analysis conditions has been handled by driving an actuator to control the valve open/close cycle and/or the duty ratio thereof. In practice, however, the driving force and the response frequency of the actuator are not good enough depending on required analysis conditions. Further, the valve element driven by the actuator travels through the fluid and receives frictional resistance from a seal member. As a result, it is difficult to move the valve element in accordance with the performance of the actuator itself (when no load acts thereon).

The present invention has been made in view of the related art. To solve the problems of the related art, an object of the present invention is to provide a pressure control apparatus for a supercritical fluid in which variation in pressure is small even in measurement in which analysis conditions are changed with time to improve separation and other performance.

Means to Solve the Problem

The present inventors have conducted extensive studies to achieve the object and found that in an openable and closable valve-based pressure control apparatus used in a supercritical fluid system (SFE/SFC), providing means for adjusting a movable range or the stroke of a valve element to an appropriate value to control the valve-opening rate allows variation in pressure to be suppressed during the use of the system, whereby an extract can be stably recovered in the SFE and chromatogram measurement can be precisely made in the SFC. The present invention has been thus attained.

That is, the pressure variation produced when the valve is opened or closed can be reduced by not only moving the valve element back and forth at all times but also appropriately adjusting the valve-opening rate.

That is, a pressure control apparatus for a supercritical fluid according to the present invention includes:
(a) a valve comprising;
  (1) a valve chamber provided in a middle of a channel through which a supercritical fluid passes, and
  (2) an electrically-operated valve element located in the valve chamber, wherein a front end of the valve element fits into the valve chamber when the valve is closed, and it travels backward when the valve is opened;
(b) a pressure detection member for detecting the pressure of the supercritical fluid in the channel on an upstream or downstream side of the valve chamber;
(c) an open/close control member for controlling the pressure detected by the pressure detection member to be a target pressure; and
(d) a valve-opening ratio adjustment member for adjusting valve-opening ratio when the valve is opened based on state of the supercritical fluid.

In the apparatus described above, the valve-opening ratio adjustment member preferably includes
(e) a backward travel restricting section that restricts the valve element from traveling backward to limit the backward travel distance of the valve element when the valve is opened, and
(f) a backward travel specifying section that specifies an optimum valve-opening ratio and instructs the backward travel restricting section of the specified optimum valve-opening ratio.

In the apparatus described above, the valve-opening ratio adjustment member preferably includes a piezoelectric actuator, and the piezoelectric actuator preferably expands or contracts to adjust the backward travel of the valve element when the valve is opened.

In the apparatus described above, the valve-opening ratio adjustment member preferably includes a table representing the relationship of at least one of pressure, flow rate and composition of the supercritical fluid, and a gap length when the valve is opened.

The gap length corresponds to a concept for mechanically-quantifying the valve-opening rate. As will hereinafter be described in detail, usually, the longer the gap length, the larger the valve-opening rate. The shorter the gap length, the smaller the valve-opening rate.

In the apparatus described above, when the detected pressure deviates from the target pressure, the valve-opening ratio adjustment member preferably automatically adjusts a gap length to an optimum value so as to minimize the difference between the detected pressure and the target pressure.

In the apparatus described above, the valve-opening ratio adjustment member preferably monitors variation in the detected pressure and automatically adjusts the gap length to an optimum value so as to minimize the variation.

Effect of the Invention

As described above, according to the present invention, providing valve-opening ratio adjustment member for adjusting the valve-opening ratio when the valve element is fully traveling backward and setting the valve-opening ratio to a value corresponding to analysis conditions allow variation in pressure to be reduced.

DESCRIPTION OF REFERENCE NUMBERS

Figure 1:
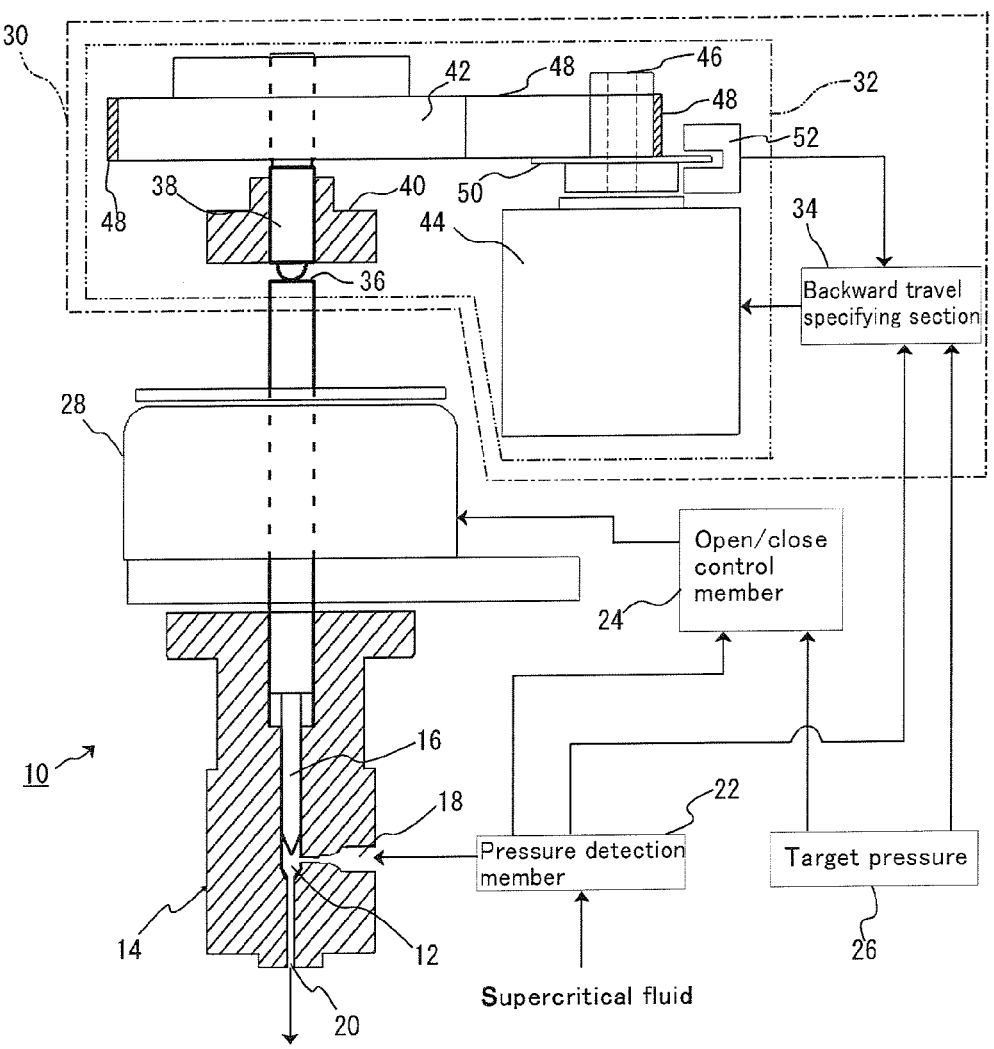
FIG. 1 describes a pressure control apparatus for a supercritical fluid according to an embodiment of the present invention in a fully open state.

10 Pressure control apparatus
12 Valve chamber
16 Valve element
18 Entrance channel
20 Exit channel
22 Pressure detection member
24 Open/close control member
30 Valve-opening ratio adjustment member
32 Backward travel restricting section
34 Backward travel specifying section
36 Tail end of valve element
38 Variable shaft
40 Variable shaft holder
42 Pulley
44 Motor
46 Rotary shaft
48 Link belt
50 Positioning plate
52 Position sensor
54 Plunger
56 Return spring 58 Seal member
60 Valve seat
62 Head
64 Set screws
100 Heating member
102 Tubular heat exchanger block
104 Pipe
106 Pipe entrance
108 Pipe exit
110 Cartridge heater
112 Cover
114 Temperature sensor
120 Stand
122 Recovery container
124 Discharge port
126 Acrylic cover
202 Liquefied carbon dioxide cylinder
204 Liquefied carbon dioxide delivery pump
206 Organic solvent
208 Modifier solvent delivery pump
210 Preheating coil
212 Injector
214 Column
216 Detector
218 Pressure control apparatus
220 Temperature control member
302 Supercritical fluid delivery section
304 Modifier delivery section
306 Accumulator
308 Injector
310 Sample injecting section
312 Column
314 Sample separator section
316 Detector
318 Pressure control apparatus
320 Carbon dioxide cylinder
322 Carbon dioxide pump
324 Circulating temperature-controlled bath
326 Modifier solvent container
328 Modifier pump
330 Bypass channel section

BEST MODE FOR CARRYING OUT THE INVENTION

A preferred embodiment of the present invention will be described below with reference to the drawings.

FIG. 1 shows a schematic configuration of a pressure control apparatus for a supercritical fluid 10 according to the present embodiment.

In FIG. 1, the pressure control apparatus 10 includes a valve body 14 in which a valve chamber 12 is formed, a valve element 16 that fits into the valve chamber 12 in the valve body 14 in an airtight manner, and an entrance channel 18 and an exit channel 20 that communicate with the valve chamber 12.

When the valve element 16 is lifted (the state shown in FIG. 1), the entrance channel 18, the valve chamber 12, and the exit channel 20 communicate with each other, and a supercritical fluid flows in through the entrance channel 18, passes through the valve chamber 12, and flows out through the exit channel 20.

Figure 2:
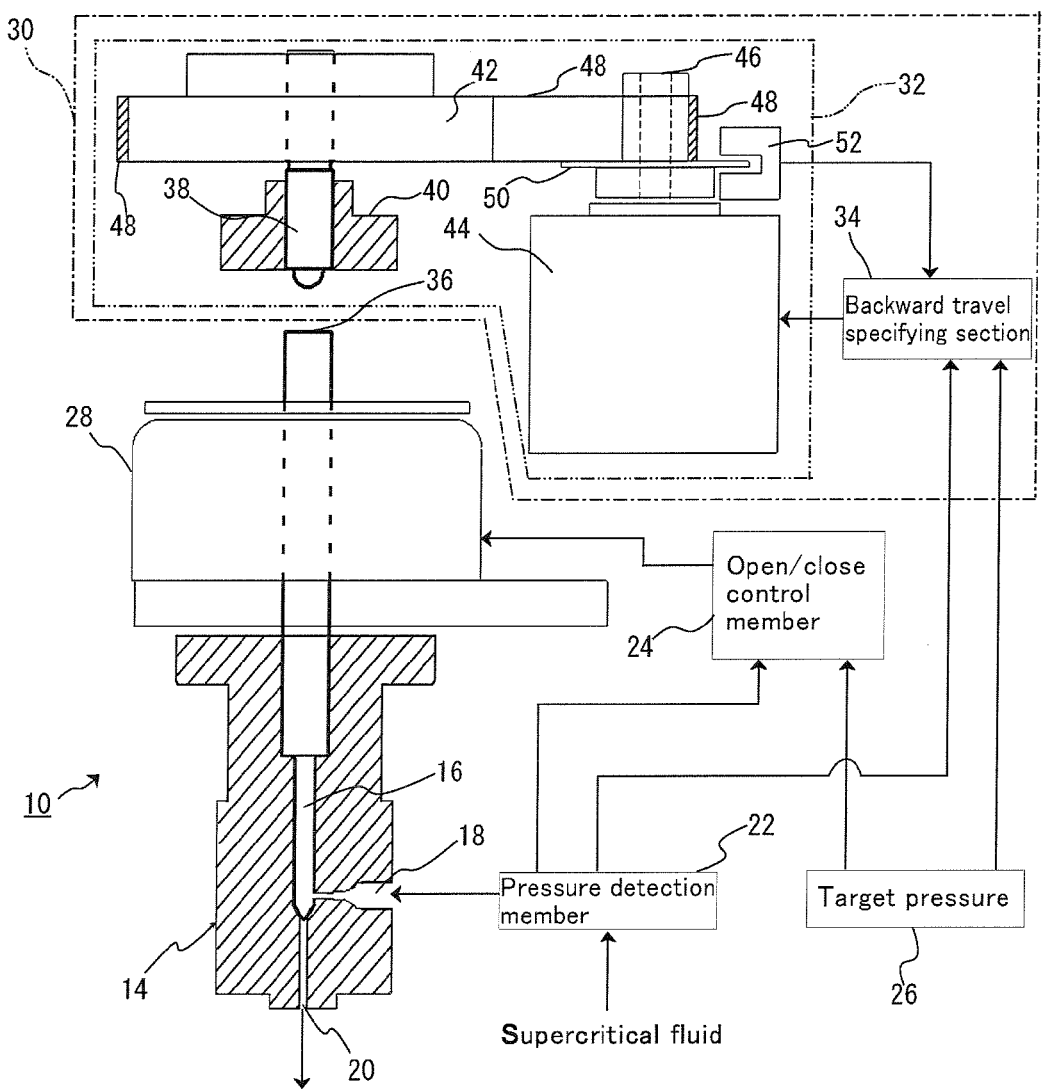
FIG. 2 describes the apparatus shown in FIG. 1 in a fully closed state.

In contrast, when the valve element 16 is lowered, as shown in FIG. 2, the front end of the valve element 16 fits into the valve chamber 12 and the channel through which the supercritical fluid passes is blocked.

In the present embodiment, the upward and downward movement of the valve element 16 is controlled by pressure detection member 22 and open/close control member 24.

That is, the pressure detection member 22 detects the pressure in the entrance channel 18, and the open/close control member 24 compares the pressure detected by the pressure detection member 22 with a preset target pressure 26 and controls the upward and downward movement of the valve element 16 in such a way that the period during which the valve element is lifted increases when the detected pressure is higher than the target pressure, whereas the period during which the valve element is lowered increases when the detected pressure is lower than the target pressure.

In the present embodiment, the valve element 16 is moved upward or downward by a solenoid 28 energized (lowering the valve element 16) or deenergized (lifting the valve element 16 with the aid of a spring that is not shown in the drawings) in response to an instruction from the open/close control member 24.

The valve open/close mechanism described above has been known in the art, and the one disclosed in Japanese Patent Publication No. 8-30989 filed by the applicant can be typically used.

Figure 3:
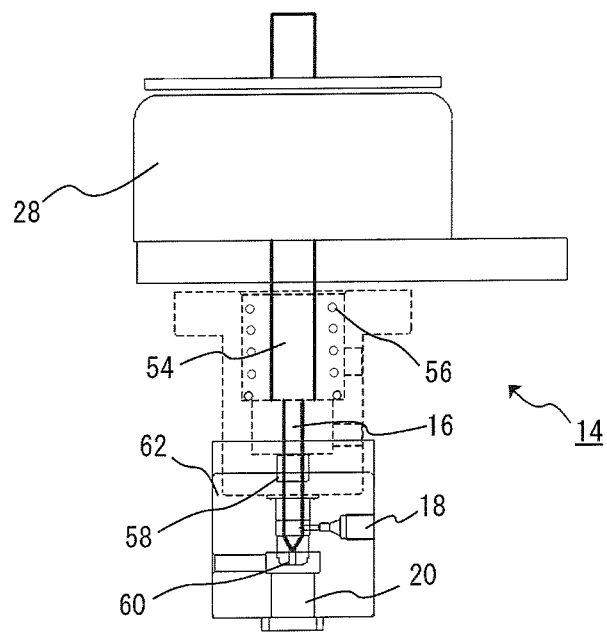
FIG. 3 describes the structure of valve body.

FIG. 3 shows the structure of the valve body 14. In the valve body 14, a plunger (of the solenoid) 54 lifts and lowers the valve element 16. The plunger 54 travels downward against a return spring 56 when the solenoid 28 is energized, whereas pushed by the return spring 56 and traveling upward when the solenoid 28 is deenergized.

In a head 62, a seal member 58 is filled in the gap between the valve element 16 and the wall of the valve chamber, and a valve seat 60 is disposed at a portion where the front end of the valve element 16 comes into contact with the exit channel 20.

The pressure control apparatus for a supercritical fluid according to the present invention is characterized in that valve-opening ratio adjustment member 30 for adjusting the valve-opening ratio is further provided in the mechanism described above. The valve-opening ratio adjustment member 30 includes a backward travel restricting section 32 that restricts the position of the valve element 16 when the solenoid 28 is deenergized and a backward travel specifying section 34. The backward travel restricting section 32 includes a variable shaft 38 that abuts a tail end 36 of the valve element to prevent the valve element from traveling backward, a variable shaft holder 40 connected to the variable shaft 38 through screw engagement, a pulley 42 that moves in coordination with the variable shaft 38, a link belt 48 (partially cross sectioned) that connects a rotary shaft 46 of a motor 44 to the pulley 42 so that they move in coordination with each other, and a positioning plate 50 and a position sensor 52 that detect the rotational position of the rotary shaft 46 of the motor.

The backward travel specifying section 34 instructs the motor 44 to rotate the rotary shaft 46 thereof by a predetermined angle and in turn rotate the variable shaft 38 via the link belt 48 and the pulley 42. As a result, the position where the variable shaft 38 engages the variable shaft holder 40 is changed, and hence the vertical position of the variable shaft 38 relative to the variable shaft holder 40 is changed. The lower end of the variable shaft 38 then abuts the tail end 36 of the valve element, as described above, preventing the valve element from traveling backward. The valve-opening rate can thus be adjusted when the valve element 16 is lifted, that is, when the valve is opened.

In the present embodiment, the stroke of the valve element 16 is adjusted when the backward travel specifying section 34 specifies an optimum valve-opening rate based on the pressure detected by the pressure detection member 22 and instructs the backward travel restricting section 32 and the variable shaft 38 adjusted to an engaged position according to the specified valve-opening rate restricts the backward travel of the tail end of the valve element. That is, when the variable shaft 38 travels downward to reduce the backward travel of the tail end 36 of the valve element (that is, reduce the backward travel of the valve element when the valve is opened), the length of the gap expressed in the stroke is shortened, and the valve-opening rate is reduced accordingly.

FIG. 1 shows a state in which the variable shaft 38 is lifted to the highest position and the stroke of the valve element is maximized. In this state, the gap between the front end of the valve element 16 and the bottom wall of the valve chamber, that is, the length of the gap, when the valve is opened can be maximized.

Figure 4:
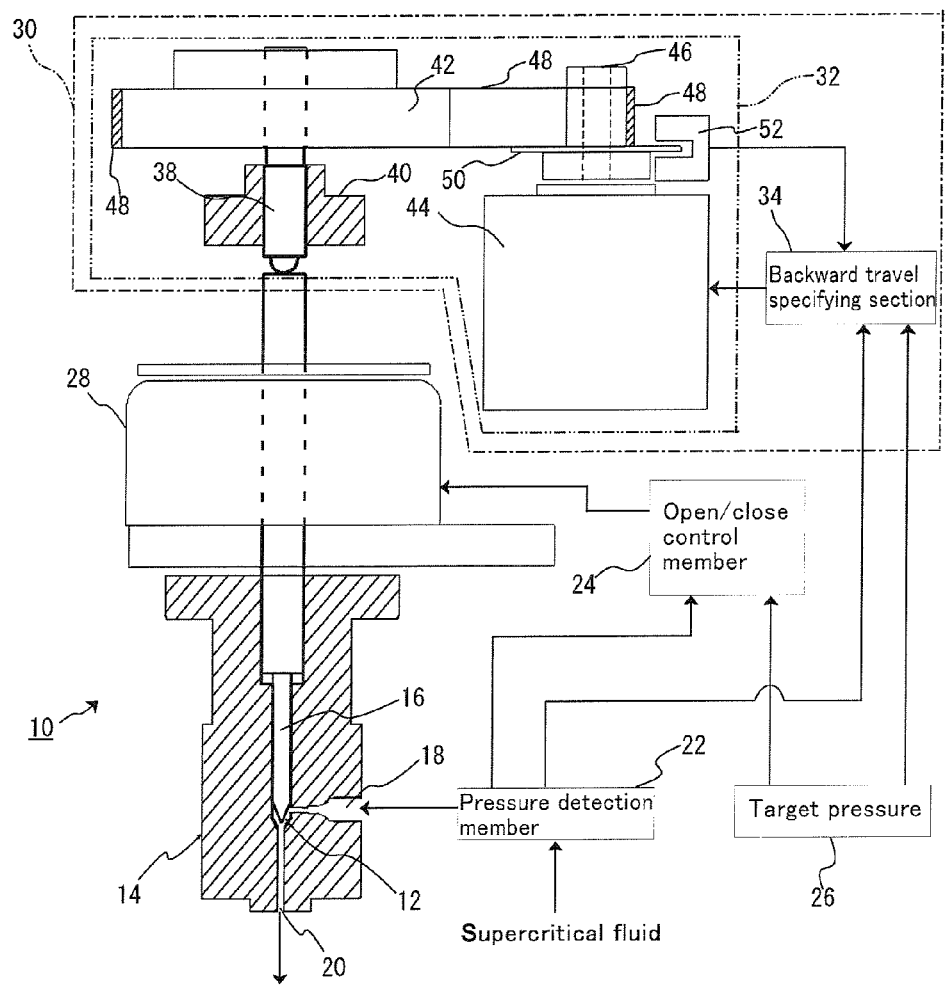
FIG. 4 shows an adjusted valve-opening ratio in the apparatus shown in FIG. 1.

In contrast, in the state shown in FIG. 4, the variable shaft 38 is lowered to the lowest position and the stroke of the valve element is minimized. In this state, the gap between the front end of the valve element 16 and the bottom wall of the valve chamber, that is, the length of the gap, when the valve is opened can be minimized.

That is, in the present embodiment, the length of the gap can be adjusted to an appropriate value by lifting/lowering the variable shaft 38 to control the stroke, which is the movable range of the valve element 16. The variable shaft 38, which determines the stroke, is lifted/lowered by the backward travel restricting section 32, which automatically adjusts the engaged position of the variable shaft in response to an instruction from the backward travel specifying section 34 according to setting conditions and variation in pressure. Since the length of the gap and the valve-opening rate are related to each other as described below, the valve-opening rate can be adjusted by controlling the length of the gap.

The valve-opening ratio adjustment carried out by the valve-opening ratio adjustment member 30 including the backward travel restricting section 32 and the backward travel specifying section 34 allows the pressure to be automatically controlled in such a way that the pressure varies only within a small range even in broad flow rate and pressure conditions that exceed the limits determined by the valve open/close cycle and the duty ratio thereof when chromatographic analysis, fractionation, or extraction using a supercritical fluid is performed by greatly changing the pressure and flow rate conditions in the course of the analysis, fractionation or extraction.

The "length of the gap" used herein is a value quantitatively expressing the gap through which a fluid can flow in or out when the valve is opened, and substantially equivalent to the travel of the valve element accompanying a valve open/close operation. That is, in the embodiment shown in FIGS. 1, 2, and 4 described above, the length of the gap is expressed in the form of the distance between the front end of the valve element 16 and the bottom wall of the valve chamber when the valve is opened (or the distance between the tail end 36 of the valve element and the lower end of the variable shaft 38 when the valve is closed) and coincides with the valve element backward travel, which is herein called the stroke.

The "valve-opening rate" determined by the gap length (stroke) described above represents how much the valve is open relative to the largest opening position when the valve is opened or is expressed by "(gap length in current opening position)/(gap length in the largest opening position)." The largest opening position corresponds to a state in which the valve is opened to the limit in a valve mechanism in use, and the gap length when the valve is opened to the limit is naturally to be the largest value in the valve mechanism. That is, in the embodiment shown in FIGS. 1, 2, and 4, the largest opening position corresponds to the state shown in FIG. 1, in which the variable shaft 38 is lifted to the highest position and the stroke (that is, the gap length) has the largest value. Since (gap length in current opening position) is equal to (gap length in largest opening position) in this state, the valve-opening rate has the largest value, which is one (100%).

On the other hand, in the embodiment shown in FIGS. 1, 2, and 4, in the state shown in FIG. 4, in which the variable shaft 38 is lowered to the lowest position and the stroke (gap length) has the shortest value, the valve-opening rate is expressed by (gap length in FIG. 4)/(gap length in FIG. 1) and has the smallest value.

Adjustment of Valve-Opening Rate

Figure 5:
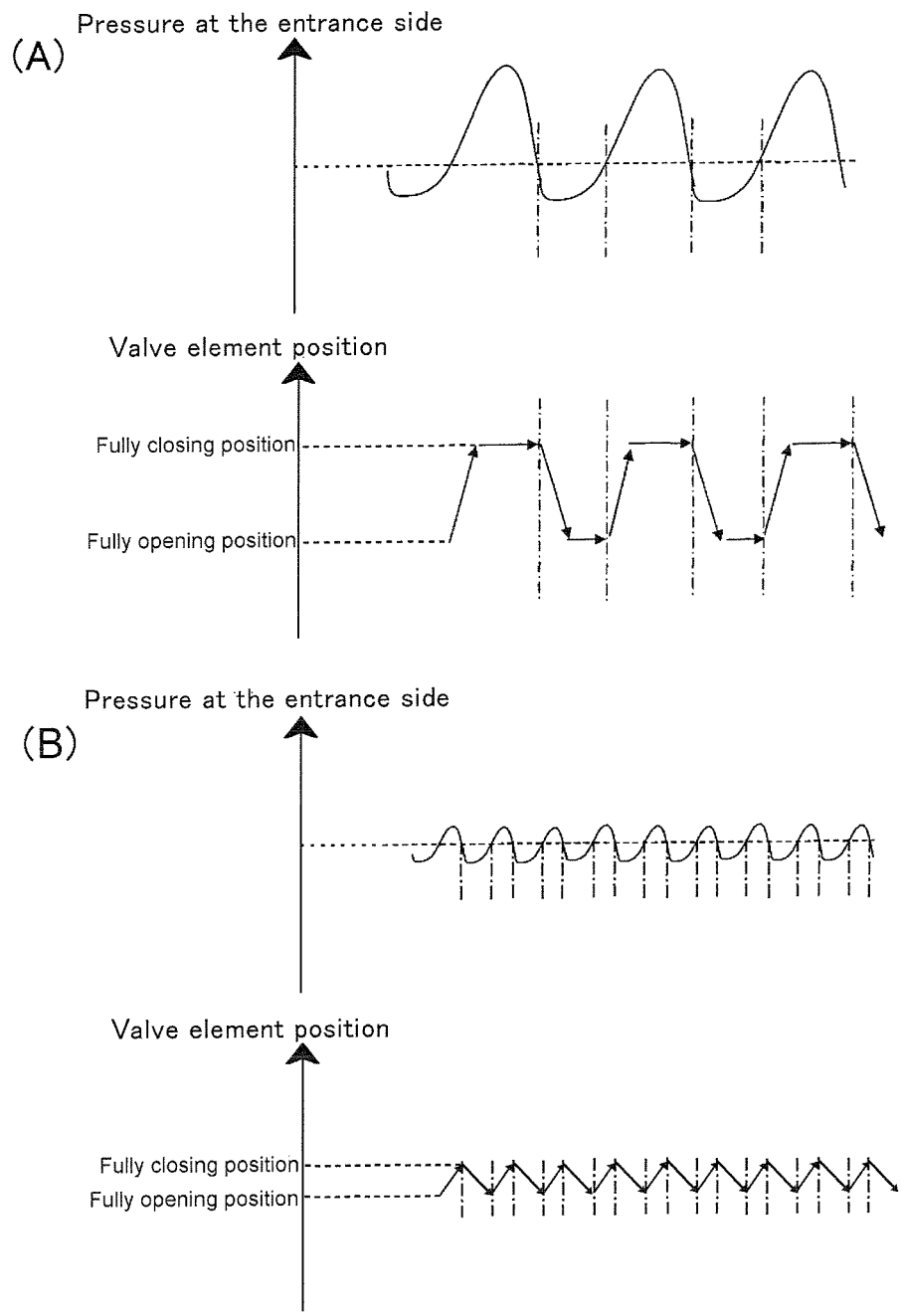
FIGS. 5(A) and 5(B) describe variation in pressure accompanying forward and backward movement of a valve element.

FIGS. 5(A) and 5(B) are graphs representing the change in the valve element position and the pressure at the entrance of the pressure control apparatus in accordance with the valve-opening rate.

FIG. 5(A) shows a state in which the stroke is excessively long with respect to a target pressure. In this case, since the stroke is long, the amount of flowing-in supercritical fluid in a single operation of fully opening/closing the valve element is relatively large. As a result, the variation in the pressure at the entrance produced when the valve is opened or closed naturally increases. That is, FIG. 5(A) shows that the pressure greatly varies although the average pressure will approach the target pressure by adjusting the open/close cycle and the duty ratio thereof. Therefore, when only adjusting of open/close cycle and the duty ratio is performed to adjust the measured pressure to the target pressure, the pressure variation is observed.

In contrast, FIG. 5(B) shows a state in which the valve-opening rate is adjusted with respect to the target pressure and the stroke is adjusted to an appropriate value. When the stroke has an appropriate value, the amount of flowing-in supercritical fluid in a single operation of fully opening/closing the valve element is smaller than that in FIG. 5(A). As shown in FIG. 5(B), the open/close cycle can be shortened, and the variation in the pressure in the apparatus can be reduced when the pressure is adjusted to the target pressure.

When the stroke is excessively short, the amount of flowing-in supercritical fluid in a single operation of fully opening/closing the valve element is excessively small. In this case, the valve cannot pass the entire predetermined amount of fluid, resulting in failure of pressure control. Even when the stroke is excessively long, as shown in FIG. 5(A), using an actuator that responds more quickly and produces a greater force conceivably allows the pressure to be adjusted to the target value and the pressure variation to be reduced. An actuator that satisfies the requirements is, however, unrealistic in consideration of the dimensions, the price, and other limiting factors. Therefore, the present inventors have determined to adjust the valve-opening rate.

In supercritical fluid chromatography, when sufficient separation is not obtained in fixed-condition analysis, or when analysis continues for a long time, the flow rate, pressure, temperature, modifier composition ratio, and other analysis conditions are changed with time to improve separation or shorten the analysis period.

In a pressure adjustment apparatus of related art incapable of adjusting the valve-opening rate during measurement, however, the pressure disadvantageously greatly varies in the apparatus when the analysis conditions are changed, as shown in FIG. 5(A).

To address the problem, in the present invention, the valve-opening fat ratio adjustment member 30 is provided to not only simply maintain the target pressure on average but also reduce the short term pressure variation.

The present inventors have conducted studies on the adjustment of the valve-opening rate and found that an optimum gap length depends on the target pressure.

Figure 7:
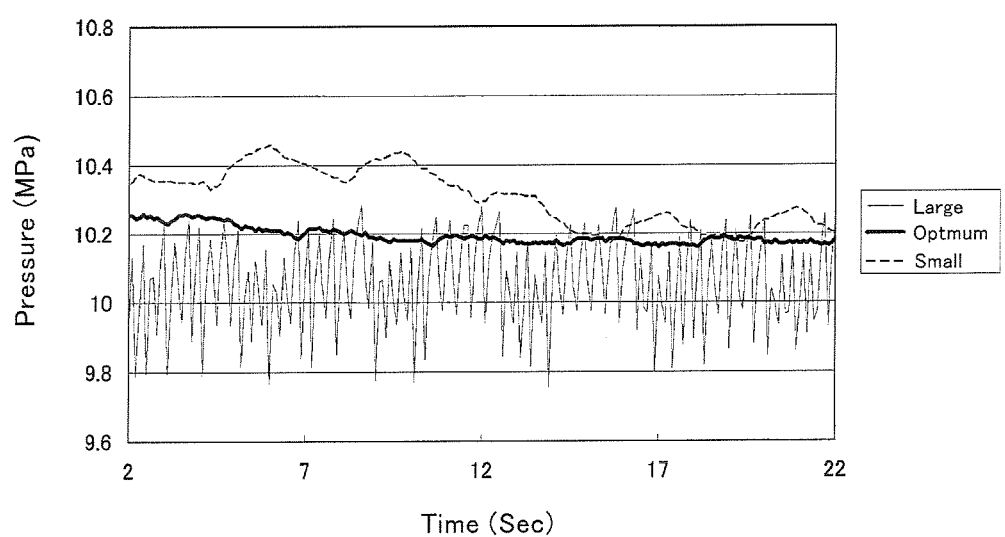
FIG. 7 describes how advantageous gap length adjustment is at a pressure of 10 MPa.
Figure 8:
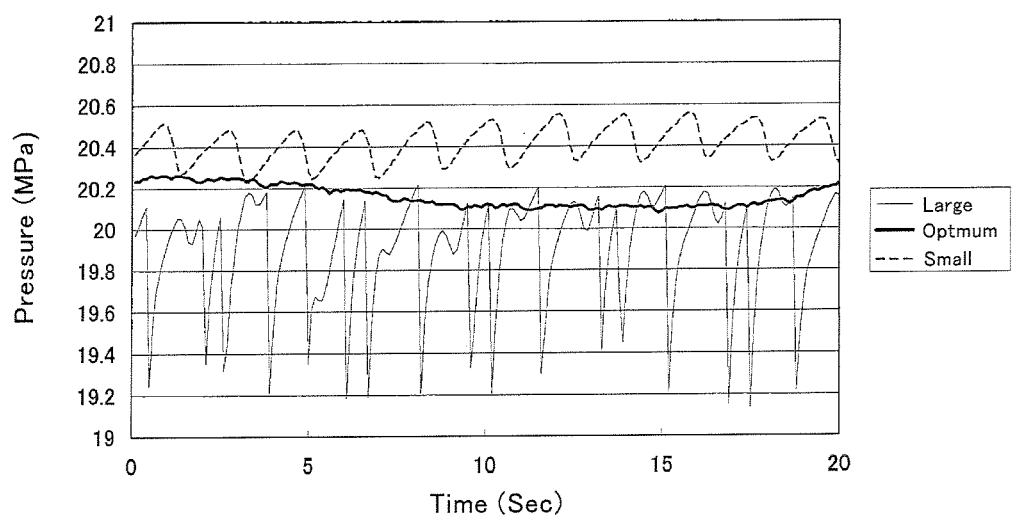
FIG. 8 describes how advantageous gap length adjustment is at a pressure of 20 MPa.
Figure 9:
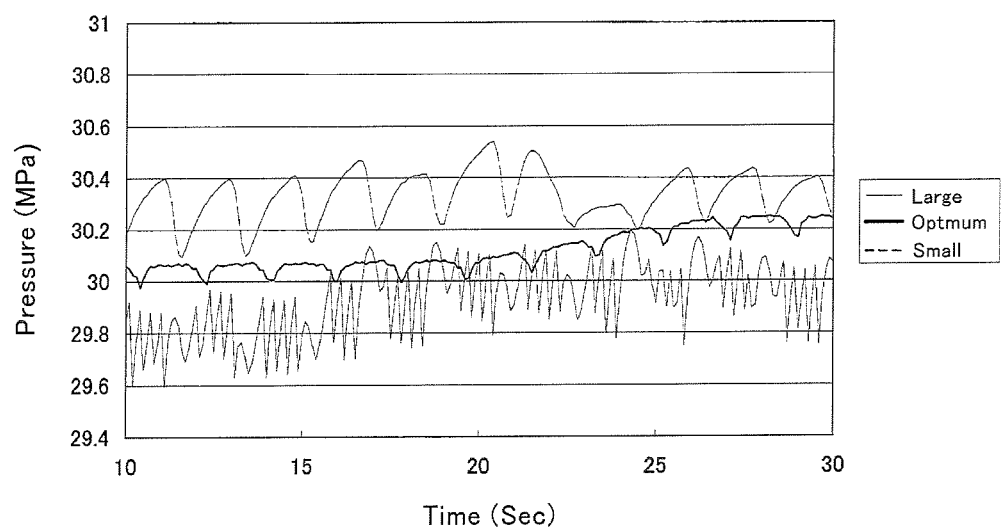
FIG. 9 describes how advantageous gap length adjustment is at a pressure of 30 MPa.

FIGS. 7 to 9 show the pressure variation in relation to how well the gap length is adjusted when the target pressure is 10 MPa, 20 MPa, and 30 MPa, respectively, allowing comparison among an optimum gap length, an excessively large gap length, and an excessively small gap length for each of the pressure values (fluid: carbon dioxide, temperature: 30° C., and flow rate: 20 ml/min).

That is, FIG. 7 shows how differently the pressure is controlled for the different gap lengths (large, optimum, and small) when the target pressure is set at 10 MPa. Similarly, FIG. 8 shows the results when the target pressure is set at 20 MPa, and FIG. 9 shows the results when the target pressure is set at 30 MPa.

As FIGS. 7 to 9 clearly show, there is an optimum gap length for each of the target pressure values, and the gap length excessively larger or smaller than the optimum gap length increases the pressure variation, resulting in decrease in pressure control precision.

Figure 6:
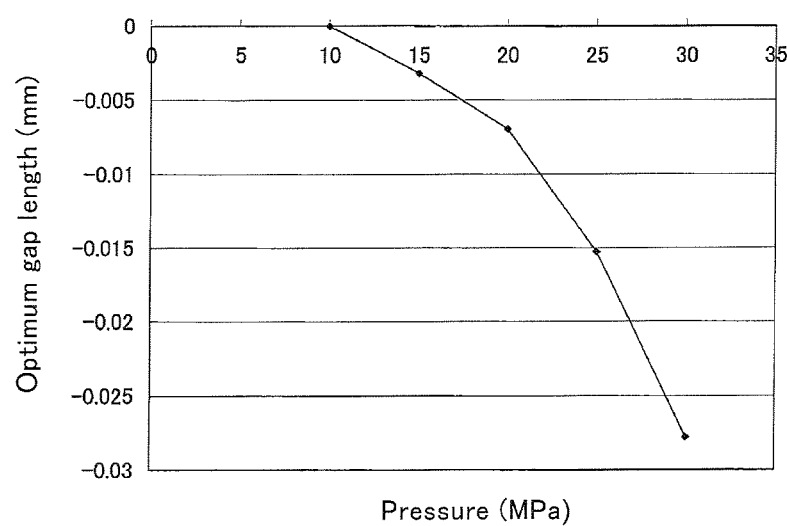
FIG. 6 describes the relationship between the pressure and an optimum gap length.
Figure 10:
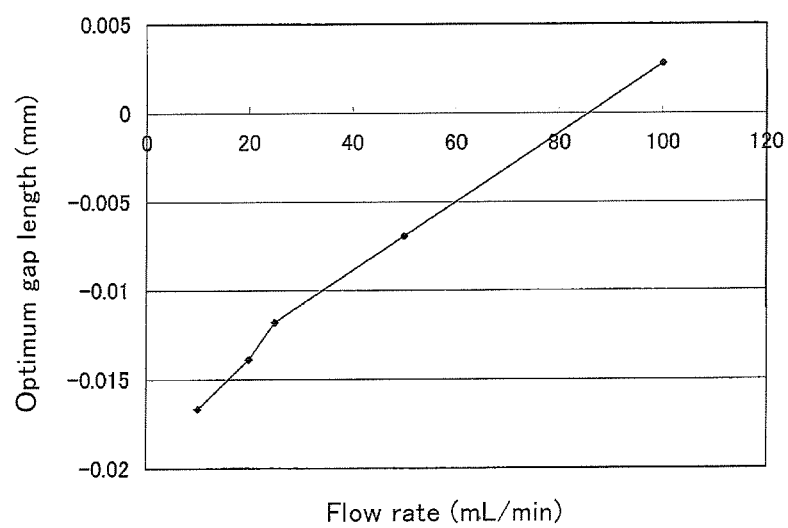
FIG. 10 describes the relationship between the flow rate and an optimum gap length.
Figure 11:
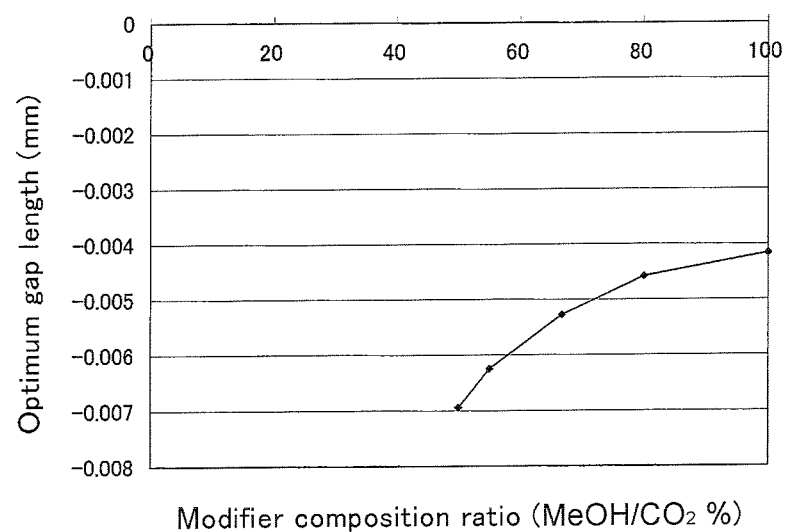
FIG. 11 describes the relationship between the solvent composition and an optimum gap length.

FIG. 6 is a graph representing the relationship between the pressure and the optimum gap length based on the results shown in FIGS. 7 to 9 and other results. The graph is drawn by using the gap length at 10 MPa as a reference and shows that the optimum gap length decreases as the pressure increases. For example, in FIG. 6, the optimum gap length at 20 MPa is smaller than the value at 10 MPa by 0.007 mm and the optimum gap length at 30 MPa is smaller than the value at 10 MPa by 0.028 mm A similar tendency is recognized in the relationship between the flow rate and the optimum gap length (FIG. 10) and the relationship between the solvent composition and the optimum gap length (FIG. 11) as well as the relationship between the pressure and the optimum gap length (FIG. 6), and the present invention is applicable to any of the relationships. The comparison among FIGS. 6, 10, and 11 clearly shows that the optimum gap length is most sensitive to the pressure change (FIG. 6).

For example, the stroke of the valve element 16 in the present embodiment may be reduced only by 0.28 mm for a large pressure change, such as 40 MPa from 10 MPa to 50 MPa. The apparatus of the present invention can thus handle a large change in the target pressure by slightly changing the gap length, which therefore requires a fairly precise control on the stroke.

To this end, in the present invention, it is preferable to connect the motor 44, which makes one turn per 200 pulses, to the pulley 42, which has a gear ratio of 10, to drive the variable shaft 38. This configuration allows a wide movable range of 25 mm with a resolution of 250 nm per pulse. FIG. 6 shows that the optimum gap length changes by 0.002 mm (2000 nm) per MPa. Since the resolution is 250 nm per pulse in the present embodiment, the target pressure can be controlled on one-MPa basis with sufficient precision. Further, the sensor used to perform the control described above is not necessarily the pressure detection member 22 but may be a flow rate sensor. Alternatively, both pressure and flow rate sensors are preferably used to perform the control based on both types of information.

Valve-Opening Rate Control Method

In the apparatus according to the present invention, the relationship between the set pressure and the optimum gap length, the relationship between the flow rate and the optimum gap length, and the relationship between the solvent composition and the optimum gap length are tabulated in advance, and the backward travel specifying section 34 can specify an optimum gap length determined by the analysis conditions.

Determining optimum gap lengths for the pressure, the flow rate, the solvent composition, and other parameters and tabulating the thus determined relationships is a cumbersome task. However, preparing the tables described above in advance eliminates a step of monitoring pressure variation and searching an optimum gap length whenever the pressure varies during measurement, whereby the response can be quick when any of the parameters is changed.

Further, when gradient control is performed on the pressure, the flow rate, the solvent composition, or any other parameter, the backward travel specifying section 34 may use data from a program used to perform the gradient control to specify the gap length.

Alternatively, an appropriate gap length may be determined by using information on the flow rate and the pressure of the fluid discharged from a pump or any other similar component. When the pressure changes, information from the pressure detection member 22 located near by the valve may not allow immediate judgment of whether the pressure has changed as programmed or has varied due to external disturbance. It therefore takes time to be stabilized the pressure when the conditions of the pump or any other similar component change. When values programmed in the pump are known in advance, the system can be stabilized more quickly by adjusting the gap length at the same time when the setting of the pump is changed. When the system is large in scale and it takes time to inform downstream components of the change in the system resulting from the change in the setting of the pump, the control is preferably performed in advance in consideration of the time difference.

When it is difficult to prepare tables corresponding to the pressure, the flow rate, the solvent composition, and other conditions, the backward travel specifying section 34 may simply compare a detected pressure with a target pressure and specify a backward travel in accordance with the difference between the detected pressure and the target pressure to adjust the gap length. For example, when the pressure difference is large, the gap length is first automatically adjusted in such a way that the difference between the detected pressure and the target pressure is minimized. The valve open/close cycle and/or the duty ratio thereof are then automatically adjusted in such a way that the pressure variation is minimized.

Alternatively, by detecting pressure variation, feedback control may be performed on a specified backward travel in such a way that the pressure variation decreases. For example, the pressure variation is controlled to be minimized by changing the valve open/close cycle and/or the duty ratio thereof with the gap length fixed. When the pressure variation exceeds a predetermined value and hence cannot be controlled with the current gap length unchanged, the open/close cycle and/or the duty ratio thereof is temporarily fixed, and a gap length that minimizes the pressure variation is then searched. Thereafter, the gap length is again fixed to the thus searched value.

In the present invention, the front end of the variable shaft 38 is shaped into a hemispherically convex portion, as shown in FIGS. 1, 2, and, 4 so that the front end may come into point contact with the tail end of the valve element. The reason for this is that when the variable shaft 38 comes into surface contact with the tail end of the valve element 16, the contact resistance increases, which may require a large driving force of the motor or may cause the valve element or the variable shaft to be inclined, resulting in variation in the gap length. Of course, the tail end of the valve element may alternatively have a convex portion for point contact.

To precisely control the valve element by using the variable shaft, it is preferable to reduce the play between the variable shaft holder 40 and the variable shaft 38 and reduce the pitch of the screw as required. In the present invention, it is particularly preferable to set the pitch of the screw at 0.5 mm/rotation or smaller.

Examples of the motor 44, which rotates the variable shaft 38 to adjust the stroke, may include a DC motor, an AC motor, a stepper motor, and any other variety of motors. In the present invention, a stepper motor is particularly preferable because it can control a required valve element movable range more precisely.

The actuator used to lift and lower the valve element 16 is not particularly limited to a specific one but can be any device that converts an electric signal into a mechanical displacement, preferably a solenoid or a piezoelectric actuator particularly in consideration of responsiveness. The frequency at which the actuator is operated may range from approximately several Hz to 100 Hz. An exemplary commercially available solenoid actuator is Model 6SFP8.3V (produced output: 250 N, response rate: 200 Hz) manufactured by SHINDENGEN ELECTRIC MANUFACTURING CO., LTD.

Figure 12:
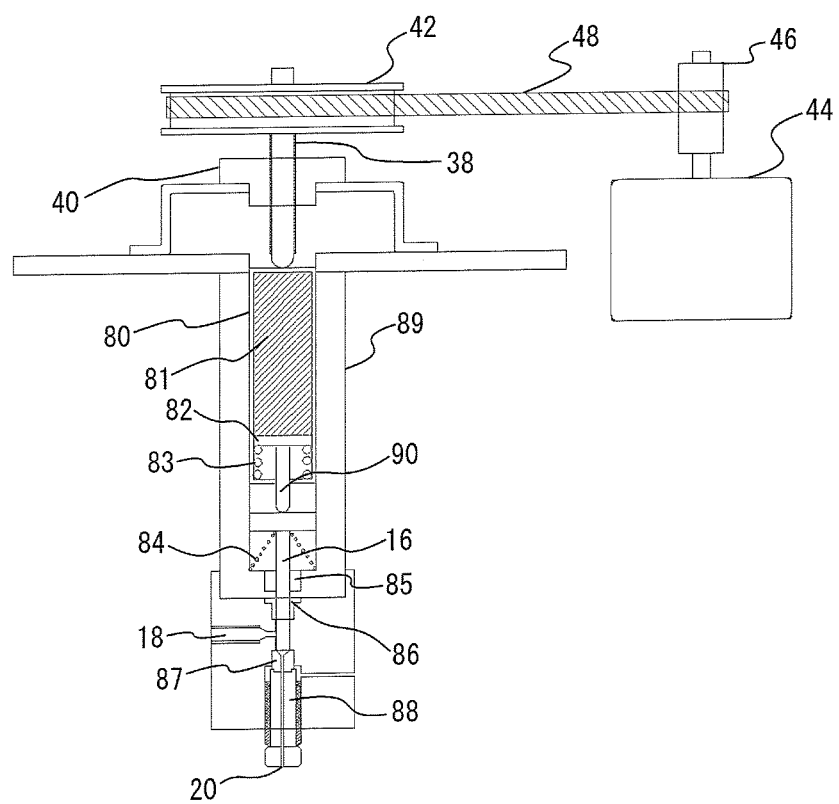
FIG. 12 shows an embodiment of the present invention in which a piezoelectric actuator is used.

FIG. 12 shows another embodiment of the present invention in which a piezoelectric actuator is used.

In FIG. 12, a piezoelectric actuator housing 80 contains a piezoelectric device 81 having a laminate structure, a piezoelectric pressure receiver 82, and a pressurizing spring 83. The piezoelectric device 81 expands and contracts in accordance with the voltage applied thereto and transfers the displacement to an actuator pin 90 via the piezoelectric pressure receiver 82. The displacement is transferred to the valve element 16 in the same manner as the embodiment shown in FIGS. 1, 2, and, 4. The piezoelectric actuator housing 80 is fixed to the variable shaft 38 and moves when the variable shaft 38 is lifted or lowered.

The piezoelectric device 81, which can control the amount of expansion by changing the applied voltage, produce a large force, and respond quickly at a rate as high as several kHz, can drive the valve element 16. An exemplary commercially available piezoelectric actuator that can be used in the present invention is Model AHB800C801POLE (total displacement: 80 μm, produced output: 800 N, response rate: 1 kHz) manufactured by NEC TOKIN Corporation.

In the embodiment shown in FIGS. 1, 2, and, 4, in which a solenoid is used as the actuator, the variable shaft, the pulley, and the motor are used to adjust the backward travel of the valve element and determine the stroke thereof. On the other hand, in the present embodiment, the piezoelectric device 81 itself can serve as the valve-opening ratio adjustment member and adjust the stroke based on the applied voltage within a displacement range of approximately 100 μm. Since the stroke of 100 μm is large enough to perform pressure control in normal usage, the variable shaft, the pulley, the motor, and other components used to adjust the backward travel are not particularly required in the embodiment in which the piezoelectric actuator is provided as the valve-opening ratio adjustment member.

To introduce a solvent into the valve for adjustment, inspection, cleaning, or other purposes, the valve may be lifted by approximately 10 mm. In consideration of such cases, the configuration described above (such as, variable shaft, pulley, and motor) may be provided as a supplemental valve-opening ratio adjustment member. The configuration described above, however, does not require precise control performance on the order of micrometer because it is simply supplementarily used to lift the valve.

In the present invention, the valve element is not limited to a specific one but may be any one that allows communication of a supercritical fluid between the entrance channel and the exit channel when the valve element is lifted, whereas blocking the communication of the supercritical fluid when the valve element is lowered. A typical valve element may be a needle-type valve element (rod valve) shown, for example, in FIGS. 1, 2, 4, and 12.

Figure 13:
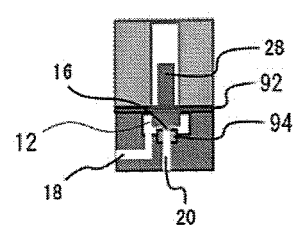
FIG. 13 shows an embodiment of the present invention in which a diaphragm-type valve element is used.

A diaphragm-type valve element may alternatively be used. A diaphragm-type valve element has a structure in which a valve element (plug) 16 is embedded in a diaphragm 92 that keeps the valve chamber 12 airtight. The entrance and exit channels are opened or closed by lifting or lowering the diaphragm 92 in response to the operation of an actuator 28 to press or separate the valve element 16 against or from a valve seat 94 disposed in the exit channel 20 in the valve chamber (FIG. 13). When the needle-type valve element shown in FIGS. 1 and 2 is used, it is preferable to fill the gap between the valve element and inner wall of the valve chamber with a seal member for keeping the gap airtight, but the seal member may wear due to friction produced by the valve element when the needle-type valve is opened and closed. In contrast, when a diaphragm-type valve element is used, no seal member for filling purposes described above is necessary because the diaphragm keeps the valve airtight. In this case, since no frictional resistance resulting from the seal member is produced, the valve can be opened and closed more quickly, whereby the pressure variation can be reduced. Further, using a diaphragm-type valve element allows the portion other than the valve element to be reduced in size. A very small, high-performance valve can therefore be provided by combining the valve element described above with a piezoelectric actuator, which is also a space-saving component. Further, the apparatus operates quietly because no collision between the tail end of the valve element and the variable shaft occurs unlike the case where a valve rod is used.

In an embodiment shown in FIG. 3 in which the valve body 14 is formed by connecting the valve element 16 to the plunger 54 of the solenoid, the seal member 58 is embedded in the immediate vicinity of the channel through which the valve element 16 operates. The seal member 58 can not only seal the fluid but also adjust the axis of the valve element 16 when the valve element 16 in close contact with the seal member 58 is driven.

In the embodiment shown in FIG. 3, the valve element 16 is driven in such a way that the excited solenoid 28 moves the valve element 16 in the front end direction, whereas the return spring 56 moves the valve element 16 in the tail end direction. If the axis of the valve element 16 does not coincide with the axis of a hole passing through the seal member 58, the resultant frictional resistance may prevent the return spring 56 from working adequately or the excited solenoid from moving the valve element 16. It is therefore important to constrain the axis of the valve element 16 so that it coincides with the axis of the hole in the seal member 58.

When a commercially available solenoid is used, fixing the valve element without care to a plunger of the solenoid may make it difficult to align the axis of the plunger with the axis of the hole in the seal member. Thus, the axis of the valve member 16 also tends to deviate. In such case, the axis of the valve element can be adjusted to coincide with the position of the hole in the seal member by joining the plunger to the valve element in the following method.

Figure 14:
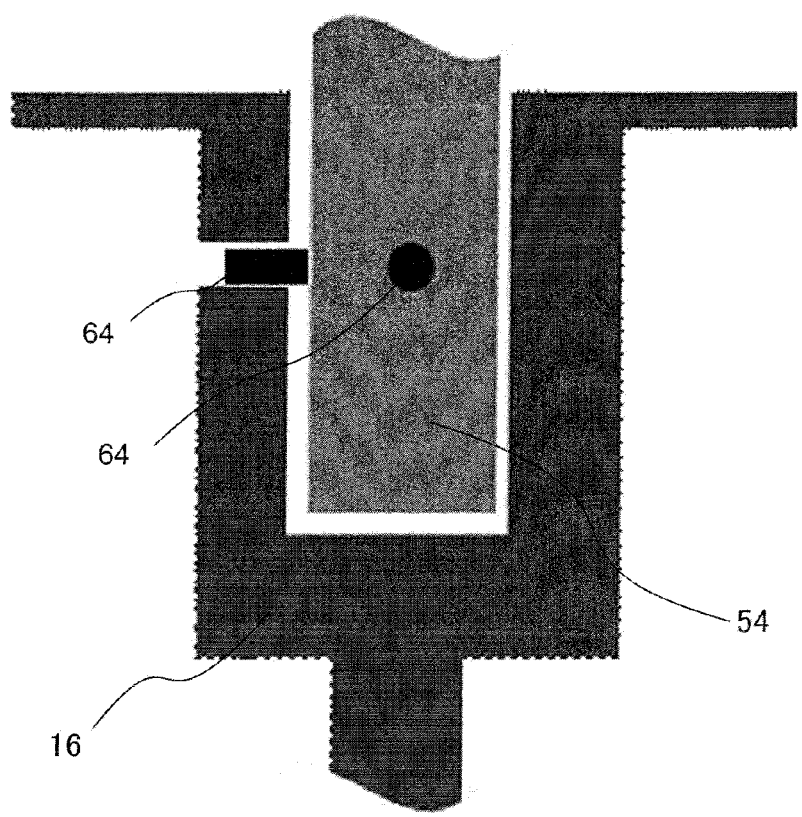
FIG. 14 shows the connection between the valve element and a plunger of the valve body shown in FIG. 3.

The method includes the steps of screwing two set screws 64 to the surface of the plunger 54 in two positions angularly spaced apart by 90 degrees to join the valve element 16 to the plunger 54, as shown in FIG. 14. It is preferable to provide a slight play at the joint between the plunger 54 and the valve element 16 so that the position of the plunger 54 fixed with the set screws 64 can be adjusted. The method allows the axis of the valve element (valve shaft) to coincide with the axis of the hole in the seal member even when the axis of the plunger does not coincide with the axis of the hole in the seal member, whereby the frictional resistance is hard to occur.

However, since the adjustment of axis of the valve element by using the set screws requires extreme precision in the method described above, a skilled technician preferably makes the adjustment. Further, the task to be done with precision is required to be carried out whenever the seal member, which is a consumable part, is replaced.

Figure 15:
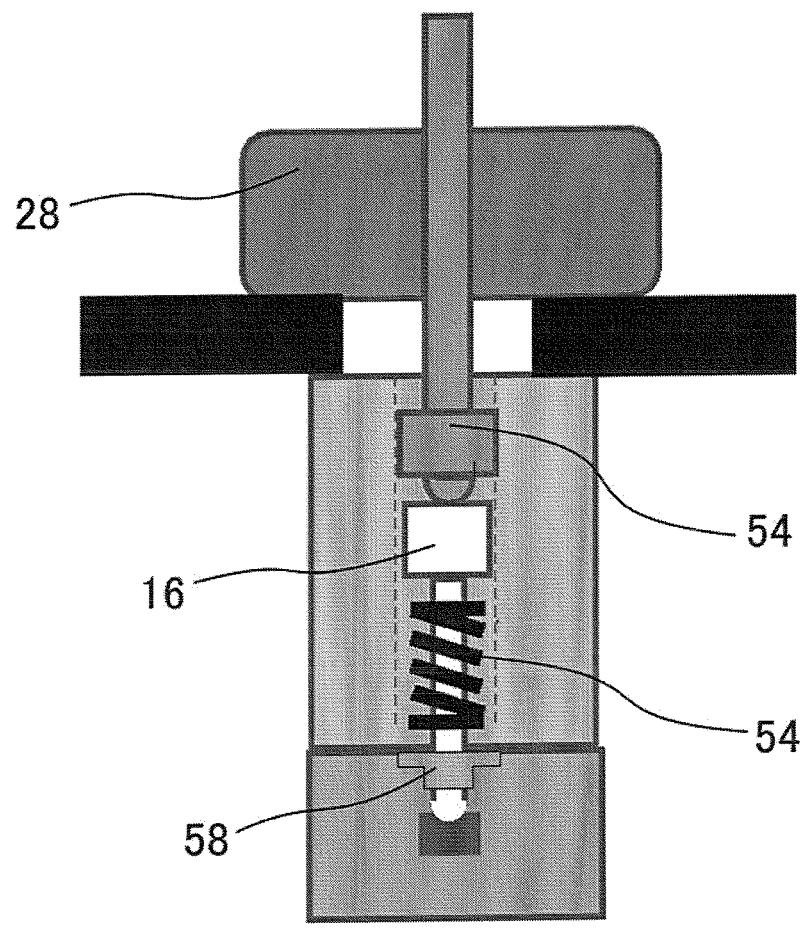
FIG. 15 shows an embodiment of the present invention in which a solenoid is used.

On the other hand, another type of the valve body can be applied to the present invention, which the front end of the plunger 54 is preferably formed of a convex curved surface, the tail end of the valve element 16 is preferably formed of a flat surface, and the plunger 54 and the valve element 16 are not preferably fixed to each other in the portion where they come into contact with each other. According to the embodiment shown in FIG. 15, the force produced when the plunger 54 moves in the front end direction is transferred to the valve element 16 through a single point on the front end of the plunger 54. Since the plunger 54 is not fixed to the valve element 16 then, the axis of the plunger 54 will not affect the axis of the valve element 16. And the axis of the valve element 16 is automatically adjusted by the action of the seal member 58 in such a way that the axis of the valve element 16 always coincides with the axis of the hole in the seal member 58. Therefore, according to the embodiment, the amount of wear of the seal member decreases, and no cumbersome adjustment using the set screws is necessary.

In the embodiment described above, the same advantageous effect can be provided when the front end of the plunger 54 is formed of a flat surface and the tail end of the valve element 16 is formed of a convex curved surface.

In the pressure control apparatus for a supercritical fluid according to the present invention, heating member can also be disposed in a downstream portion of the apparatus.

In a supercritical fluid extraction system (SFE) using a supercritical fluid, an extract is recovered by releasing the pressure in a downstream portion of an adjusting valve mechanism, such as the pressure control apparatus according to the present invention, and vaporizing only a mobile phase fluid. An extract is typically recovered in a recovery container connected to the valve mechanism with an appropriate pipe. At this point, since the fluid having undergone the pressure release process in the adjusting valve mechanism abruptly expands and absorbs heat, the pipe and the recovery container through which the fluid passes are greatly cooled, resulting in condensation and frost in some cases.

The resultant dews and ice blocks produced when the dews freeze may cause the following problems:
    Handling problem caused by the resultant drench around the pipe,
    Performance problem caused by decrease in extract purity due to the water contaminating the recovered substance, and
    Safety problem caused by destruction of the container due to clogging of an exhaust port of the recovery container and the resultant increase in the inner pressure in the container.

To address the problems described above, it is preferable to dispose heating member in a downstream portion of the apparatus according to the present invention to mitigate condensation and frost in the pipe and the recovery container.

Figure 16:
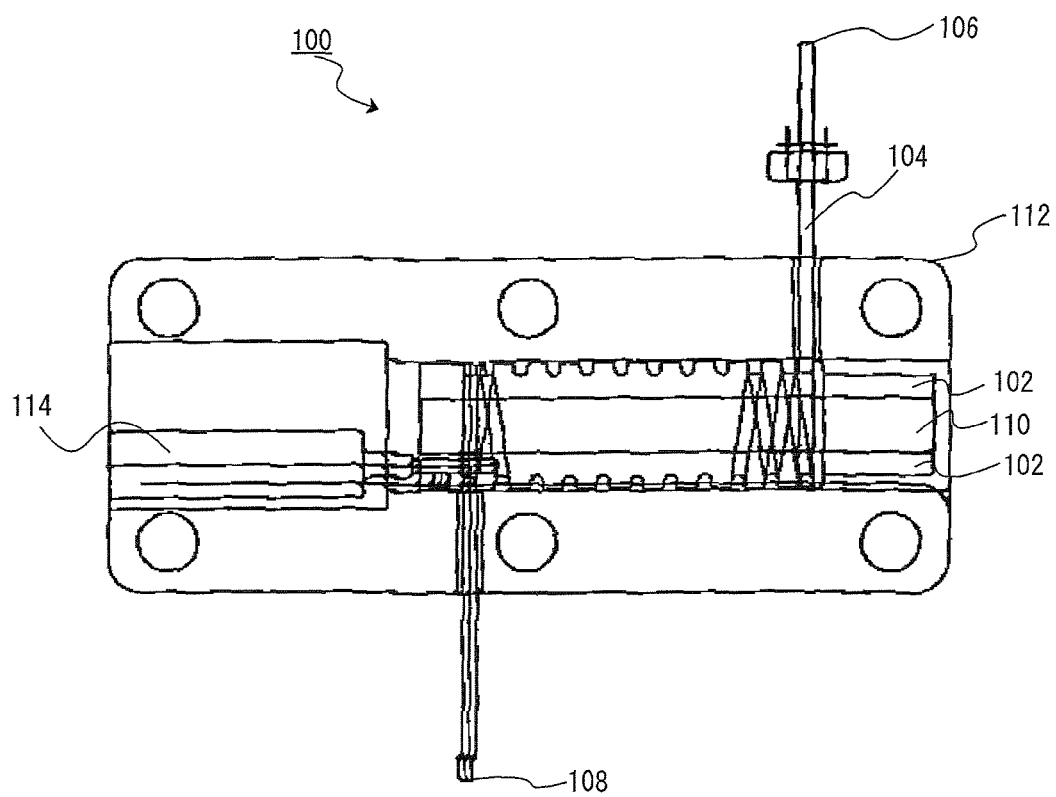
FIG. 16 is a cross-sectional view showing exemplary heating member that can be used in the present invention.

FIG. 16 is a cross-sectional view showing an example of the heating member.

In FIG. 16, heating member 100 has a structure in which a stainless steel pipe 104 is wound around a tubular heat exchanger block 102 made of aluminum or any other suitable conductor. An entrance 106 of the pipe 104 is connected to the exit channel 20 of the pressure control apparatus 10 according to the present invention described above, and vaporized fluid discharged through the exit channel 20 passes through the pipe 104 and reaches an exit 108. The pipe exit 108 can be connected to the recovery container in which an extract in the fluid is recovered. A cartridge heater 110 is incorporated in the tube of the heat exchanger block 102, and the heat generated by the heater is transferred through the heat exchanger block to the pipe therearound and heats the vaporized fluid passing through the pipe.

The heat exchanger block 102, around which the pipe 104 is wound, may be covered with a cover 112 made of Teflon® or any other suitable material in consideration of heat insulation and ease of attachment. Further, a temperature sensor 114 may be attached to the vicinity of the exit 108 of the pipe of the heating apparatus 100, and the heating temperature of the heating apparatus 100 may be controlled based on the sensed temperature of the pipe. In this case, the control is preferably performed in such a way that the temperature in the vicinity of the pipe exit 108 is kept approximately at room temperature.

In the heating member, the diameter and the length of the pipe 104 and the number of turns of the pipe 104 around the heat exchanger block may be determined as appropriate based on the analysis conditions, the characteristics of an extract, and other conditions.

Figure 17:
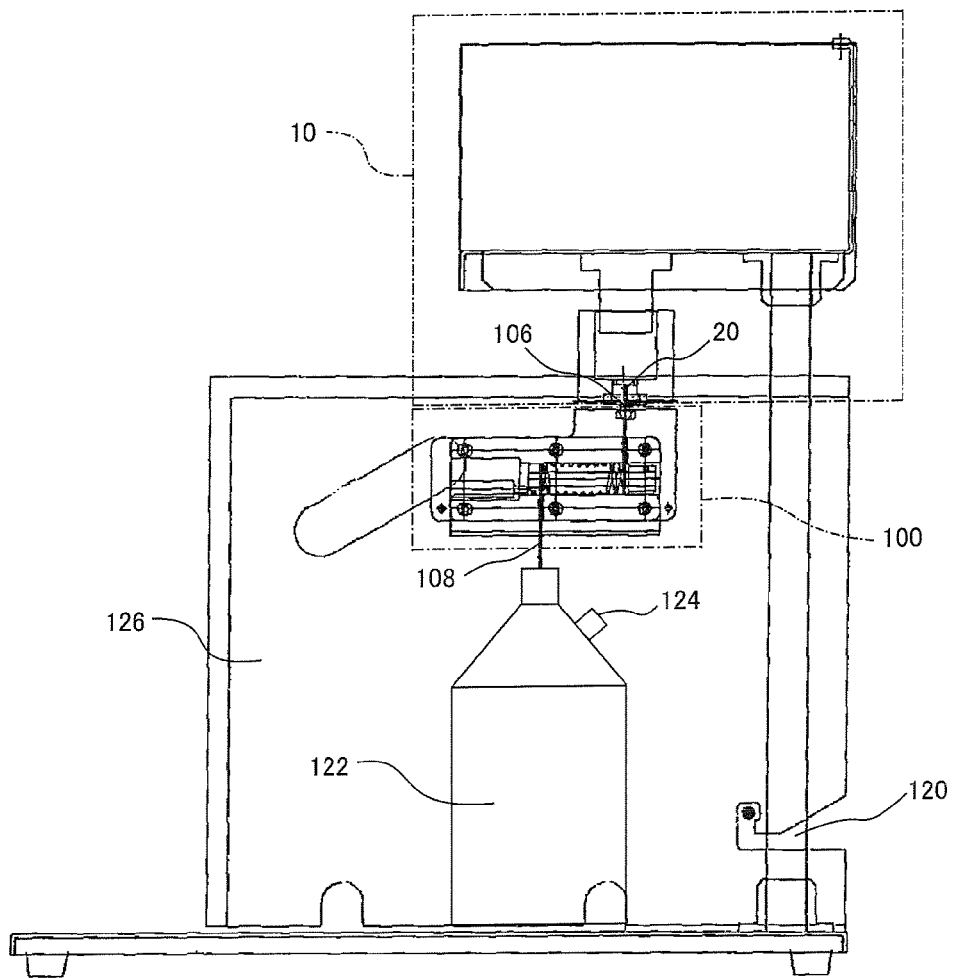
FIG. 17 shows an exemplary configuration of the pressure control apparatus for a supercritical fluid according to the invention combined with heating member.

FIG. 17 shows an exemplary configuration of the pressure control apparatus for a supercritical fluid according to the invention combined with the heating member.

In FIG. 17, the pressure control apparatus 10 is supported on a stand 120 formed of a base and a supporting column. The heating member 100 is fixed to the pressure control apparatus 10 as appropriate, and the pipe entrance 106 of the heating member 100 is connected to the exit channel 20 in a lower portion of the pressure control apparatus. The pipe exit 108 of the heating member 100 is connected to the entrance of a recovery container 122, and an extract along with a mobile phase fluid flowing out of the pressure control apparatus 10 is recovered in the recovery container 122. The recovery container 122 has a discharge port 124 for discharging a vaporized mobile phase fluid.

When carbon dioxide is used as the supercritical fluid, dry ice is produced in some cases due to adiabatic expansion in the exit path of the pressure control apparatus. The dry ice may enter the glass recovery container and expand when vaporized, resulting in breakage of the container in some cases. On the other hand, since the fluid is discharged in the form of aerosol from the pressure control apparatus, the entire discharged fluid is hardly trapped but part thereof is inevitably diffused out of the system. It is therefore necessary to take measures to ensure the safety of an operator when a harmful extract is recovered.

To protect the operator from possible breakage of the recovery container and a harmful extract spattered therefrom, the fluid path downstream of the exit of the pressure control apparatus 10 can be covered with an acrylic cover 126, as shown in FIG. 17. In particular, a transparent acrylic cover that allows the operator to view extract recovery all the time is preferably used.

A supercritical system (SFE/SFC) in which the pressure control apparatus according to the present invention is used is not particularly limited to a specific one, and may, for example, be the following SFC including temperature control member for adjusting the density of the fluid in a column.

SFC using a supercritical fluid as the mobile phase may be problematic, as compared with high performance liquid chromatography (HPLC) or ultra high performance liquid chromatography (UHPLC) using a liquid as the mobile phase, in that a slight change in pressure of the mobile phase greatly changes the density of the fluid in the system. The change in density in an SFC column greatly affects the elution performance of the supercritical fluid and hence prevents stable measurement.

In particular, in SFC using a microbead packed column, temperature control performed across the column in a conventional manner may create a difference in pressure between the entrance and the exit of the column, resulting in change in the density. In this case, the column may not exhibit its designed performance in some cases. That is, the density of the mobile phase changes with the pressure of the mobile phase in the column, and the elution power disadvantageously changes in a continuous manner.

It is therefore preferable to use temperature control member that provides a temperature gradient in which the temperature at the entrance of the SFC column is higher than the temperature at the exit thereof so as to avoid or reduce any density change produced in the column.

Figure 18:
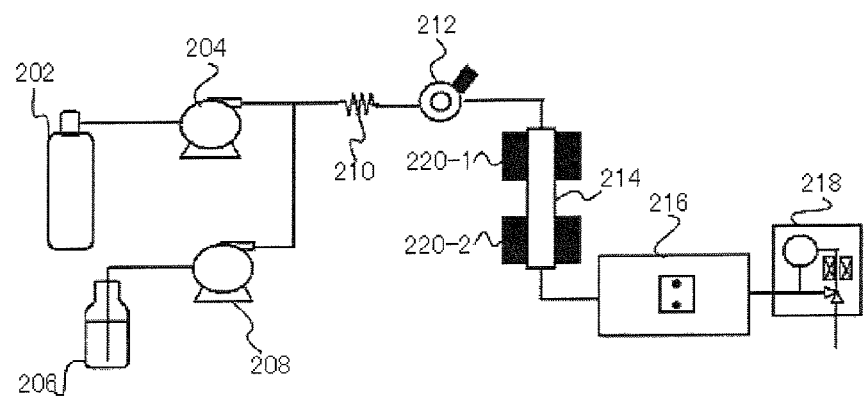
FIG. 18 shows an exemplary configuration of supercritical fluid chromatography including temperature control member that provides a temperature gradient between the entrance and the exit of a column.

FIG. 18 shows an exemplary configuration of SFC including the temperature control member.

In FIG. 18, liquefied carbon dioxide delivered from a liquefied carbon dioxide cylinder 202 through a channel to a liquefied carbon dioxide delivery pump 204 is pressurized by the pump and a pressure control apparatus 218 into a supercritical fluid having a critical pressure or higher. At the same time, an organic solvent 206, which is a supplemental solvent (modifier), is delivered to a modifier solvent delivery pump 208, is pressurized therein, merges with the supercritical fluid described above, and is mixed therewith. The mobile phase fluids are heated by a preheating coil 210 to a temperature higher than or equal to the critical temperature, dissolves a sample introduced from an injector 212, and is introduced into a column 214 filled with microbeads.

Temperature control members 220-1 and 220-2 are disposed at the entrance and the exit of the column 214 respectively, and set in such a way that the temperatures at the entrance and the exit are higher than or equal to the critical temperature of the mobile phase and the temperature at the entrance is higher than the temperature at the exit.

That is, the mobile phase, which has been heated to the critical temperature or higher by the preheating coil 210 and to which a sample has been introduced, is heated (by heating the entrance of the column 214 with the temperature control member 220-1) and then flows into the column. Thereafter, the mobile phase is further heated by the exit-side temperature control member 220-2 to a temperature lower than that of the member 220-1 or cooled and flows out of the column. As a result, a temperature gradient between the entrance and the exit of the column 214 in which the temperature at the entrance is higher than the temperature at the exit is produced.

Each component of the sample dissolved in the mobile phase and separated in the column 214 is eluted in the column and delivered to a detector 216 for detection. The pressure in the system configured as described above during the measurement is maintained by the pressure control apparatus 218 to be greater than or equal to the critical pressure of the mobile phase.

The configuration shown in FIG. 18 is presented by way of example, and any type of temperature control member can be used and disposed in any location as long as it can produce a similar temperature gradient across the column used to separate components.

In addition to the above, another example of the supercritical fluid system to which the present invention is applied may be the following SFC including a sample injecting section capable of lowering the ratio of a sample solvent to carbon dioxide in the mobile phase.

In typical SFC, a sample is supplied in the form of a sample solution in which the sample is dissolved in an organic solvent or any other suitable liquid, and a sample loop of the injector is filled with the sample solution. Thereafter, the sample loop is introduced into a mobile phase channel by switching a high-pressure valve of the injector. As a result, the sample solution is introduced into the channel. At this point, the pipe is filled with the sample solution, and a sample band is formed in the mobile phase channel. Since the sample solution in the form of the sample band then reaches the top of the column, the ratio of the sample solvent to the carbon dioxide in the mobile phase naturally increases to a very high value, and a leading portion appears at the elution peak in some cases.

The ratio of the sample solvent to the carbon dioxide in the mobile phase, which is obtained by combining the supercritical fluid with the modifier, is preferably lowered by disposing a bypass channel at the channel (main channel) through which the mobile phase passes toward the column top. Preferably, the bypass channel extends from an upstream portion to a downstream portion of the main channel. And the sample solution may be introduced into the main channel from a sample injection member while providing and running the mobile phase to the bypass channel.

Figure 19:
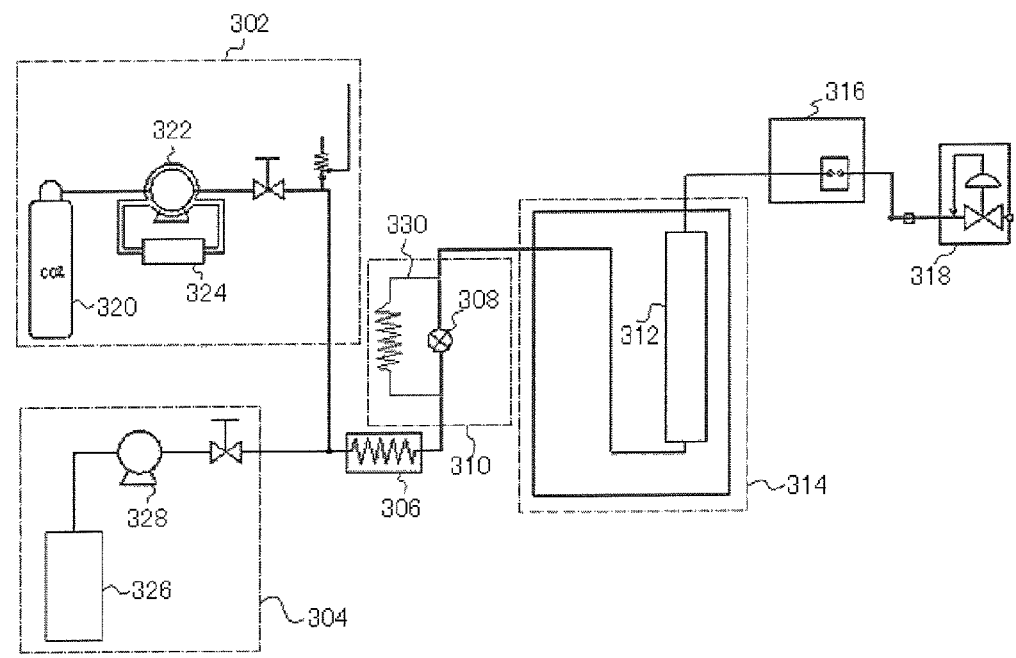
FIG. 19 shows an exemplary configuration of supercritical fluid chromatography including a sample injecting section having a bypass channel.

FIG. 19 shows an exemplary configuration of SFC including the sample injection member.

The SFC shown in FIG. 19 includes a supercritical fluid delivery section 302 that supplies a supercritical fluid, a modifier delivery section 304 that supplies a supplemental solvent, an accumulator 306 that mixes the supercritical fluid with the supplemental solvent, a sample injecting section 310 including an injector 308, a sample separator section 314 including a column 312, a detector 316, and a pressure control apparatus 318.

The supercritical fluid delivery section 302 includes a carbon dioxide cylinder 320, a pump 322 that increases the pressure of the carbon dioxide supplied from the cylinder 320, and a circulating temperature-controlled bath 324 that lowers the temperature of the carbon dioxide. The modifier delivery section 304 includes a modifier solvent container 326 and a pump 328 that increase the pressure of the modifier and delivers the pressurized modifier. The supercritical fluid and the supplemental solvent from the delivery sections 302 and 304 are combined in the accumulator 306 into a fluid having a composition ratio according to the flow rates of the fluids from the pumps 322 and 328, and supplied as the mobile phase to the sample injecting section 310. In the sample injecting section 310, the mobile phase channel described above is formed of the main channel and the bypass channel section 330 connecting an upstream portion to the downstream portion of the main channel, and the injector 308 for injecting a sample is disposed in the main channel.

In the SFC having the exemplary configuration described above, the sample is supplied in the form of a sample solution in which the sample is dissolved in an organic solvent or any other suitable liquid, and the sample loop of the injector 308 is filled with the sample solution. Thereafter, the sample loop is introduced into the mobile phase channel by switching a high-pressure valve of the injector 308. As a result, the sample solution is introduced into the channel.

At the time of sample solution injection, the supercritical fluid supplied from the supercritical fluid delivery section 302 and the supplemental solvent supplied from the modifier supplier 304 are supplied as the mobile phase combined in the accumulator 306 to both the main channel, in which the injector 308 is disposed, and the bypass channel section 330. In the configuration described above, the combined fluid formed of the sample solution in the sample loop in the main channel and the mobile phase fluid (supercritical fluid and supplemental solvent) supplied from the bypass channel is introduced into the column 312, whereby the ratio of the sample solvent to the carbon dioxide in the mobile phase can be lowered. It is therefore possible to prevent a peak from suffering a leading portion due to the solvent in which the sample is dissolved, shorten the period from the leading edge of the peak to the trailing edge thereof, and further improve the productivity of sample fractionation. The sample components eluted from the column 312 are collected in the recovery container or any other suitable container for fractionation after passing through the pressure control apparatus 318.

The configuration shown in FIG. 19 is presented by way of example, and a high-pressure valve, a variable restrictor, a temperature controller, another injector, and other components may be disposed in the bypass channel section 330 in order to suppress increase in the ratio of the sample solvent to the carbon dioxide in the mobile phase.

Figure 20:
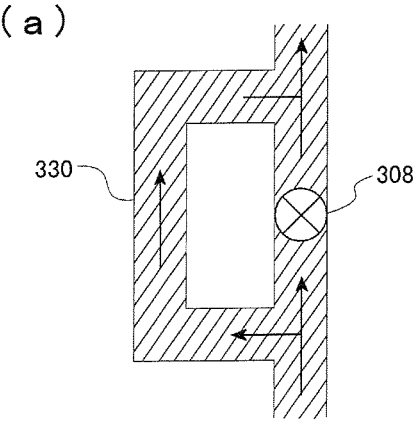
FIGS. 20(A) to 20(C) diagrammatically show sample solution injection stages in the sample injecting section in the supercritical fluid chromatography including the injecting section having the bypass channel.
Figure 20:
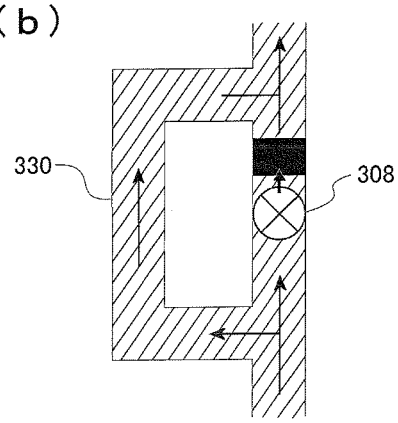
Figure 20:
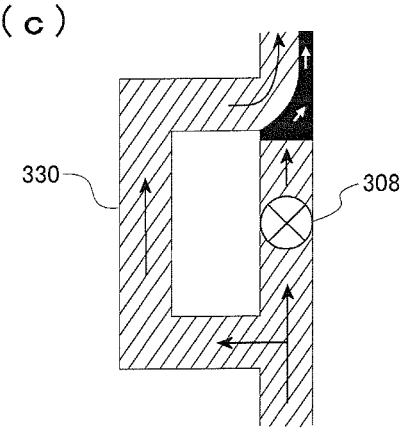

FIGS. 20(A) to 20(C) diagrammatically shows sample solution injection stages in the sample injecting section 310 in the exemplary configuration described above.

FIG. 20(A) shows the mobile phase having passed through the accumulator 306 and passing through the main channel and the bypass channel section 330 to the column. The arrows in FIG. 20(A) represent the directions in which the mobile phase flows, and the hatched lines represent the mobile phase.

FIG. 20(B) shows a state immediately after the sample solution is injected into the state shown in FIG. 20(A). That is, when the sample solution in the sample loop of the injector 308 is supplied into the mobile phase, the channel is filled with the sample solution, and a sample band shown in black in FIG. 20(B) is formed. In an apparatus with no bypass channel disposed, the sample solution in the form of the band is introduced to the column top. In this case, the solvent in which the sample is dissolved greatly affects the measurement, resulting in a leading portion during the measurement in some cases.

On the other hand, in the exemplary configuration described above in which the bypass channel is disposed, when the sample band reaches the point where the bypass channel section 330 merges with the main channel, the sample solution is combined with the mobile phase that flows in through the bypass channel, and the combined fluid is introduced into the column. The ratio of the sample solvent to the carbon dioxide in the mobile phase is therefore greatly lowered. According to the mechanism described above, SFC including the sample injection section described above can be used to suppress a leading portion resulting from the solvent in which the sample is dissolved.

The pressure control apparatus according to the present invention can be used not only in any of the supercritical fluid systems described above or a combination thereof but also in any supercritical fluid system having a configuration other than those described above.

EXAMPLES

Examples of the pressure control apparatus according to the present invention will be described below. It should be noted that the following examples are presented by way of example of the present invention and do not limit embodiments thereof.

A supercritical fluid ($CO_2$) was delivered to a supercritical fluid system to which the pressure control apparatus according to the present invention including the valve-opening ratio adjustment member was connected. The supercritical fluid was delivered in the following conditions, and the change in the pressure in the system was measured (Example 1). The start flow rate of the supercritical fluid ($CO_2$) was 20 ml/min, and the flow rate was increased linearly to 40 ml/min 1 minute after the start time. The flow rate was maintained at 40 ml/min afterward.

As Comparative Example 1, the same measurement was made for a case where a pressure control apparatus with no valve-opening ratio adjustment member was used. In Comparative Example 1, the stroke of the valve element was a fixed value suitable for the flow rate of 40 ml/min (gap length at 14.0 MPa).

Figure 21:
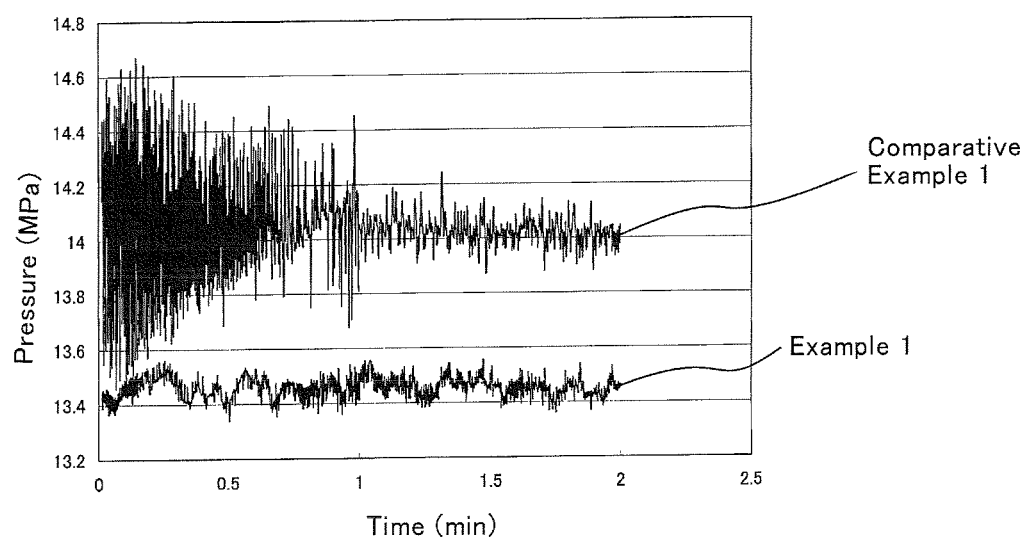
FIG. 21 shows pressure variation in Example 1 and Comparative Example 1.

FIG. 21 shows the results.

As shown in FIG. 21, in Example 1 in which the pressure control apparatus according to the present invention is used, variation in the pressure in the supercritical fluid system was significantly small. The reason for this is that the stroke of the valve element was automatically adjusted to an appropriate value by the valve-opening ratio adjustment member in response to the change in the flow rate of the supercritical fluid.

On the other hand, in Comparative Example 1, the pressure variation was particularly large in the period from 0 to 1 minute in which the stroke was not appropriately adjusted with respect to the flow rate.

A description will next be made of Reference Examples showing use of the pressure control apparatus according to the present invention in a variety of supercritical fluid systems in which the pressure control apparatus can be used. The following Reference Examples are presented by way of example of the supercritical fluid systems to which the present invention is applicable but do not limit the present invention.

Reference Example 1

In the apparatus shown in FIG. 18, in which the pressure control apparatus according to the present invention including the valve-opening ratio adjustment member was employed, carbon dioxide delivered from the liquefied carbon dioxide cylinder 202 was pressurized by the delivery pump 204 and delivered therefrom, and methanol used as the organic solvent (modifier) 206 was pressurized by the modifier solvent delivery pump 208 and delivered therefrom. The pressure in the apparatus was controlled by the pressure control apparatus 218 to 20 MPa, which is greater than the critical pressure of carbon dioxide.

The mobile phase formed of the carbon dioxide and the methanol (carbon dioxide/methanol (volume ratio)=1/0.1) delivered from the pumps was heated by the preheating coil 210 to a temperature higher than the critical temperature of carbon dioxide, and then a sample was injected from the injector 212 and dissolved in the mobile phase. The sample was a mixture of toluene, m-nitroaniline, and caffeine.

Subsequently, the mobile phase in which the sample was dissolved was introduced into the column 214 (1.8 μm-grain size silica gel column: 2.1 mm I.D.×50 mm L), and the components eluted from the column were detected by the detector 216 (UV detector).

The temperature control members disposed around the column 214 set the temperature at the entrance of the column (temperature control member 220-1) at 60° C. and the temperature at the exit (temperature control member 220-2) at 40° C. A temperature gradient of approximately 20° C. was thus produced between the entrance and the exit. The preheating coil 210 was set at 80° C. so that the temperature was well maintained in the course to the column. The pipe from the preheating coil 210 to the entrance of the column was thermally insulated so that the temperature in the apparatus did not decrease unnecessarily.

Figure 22:
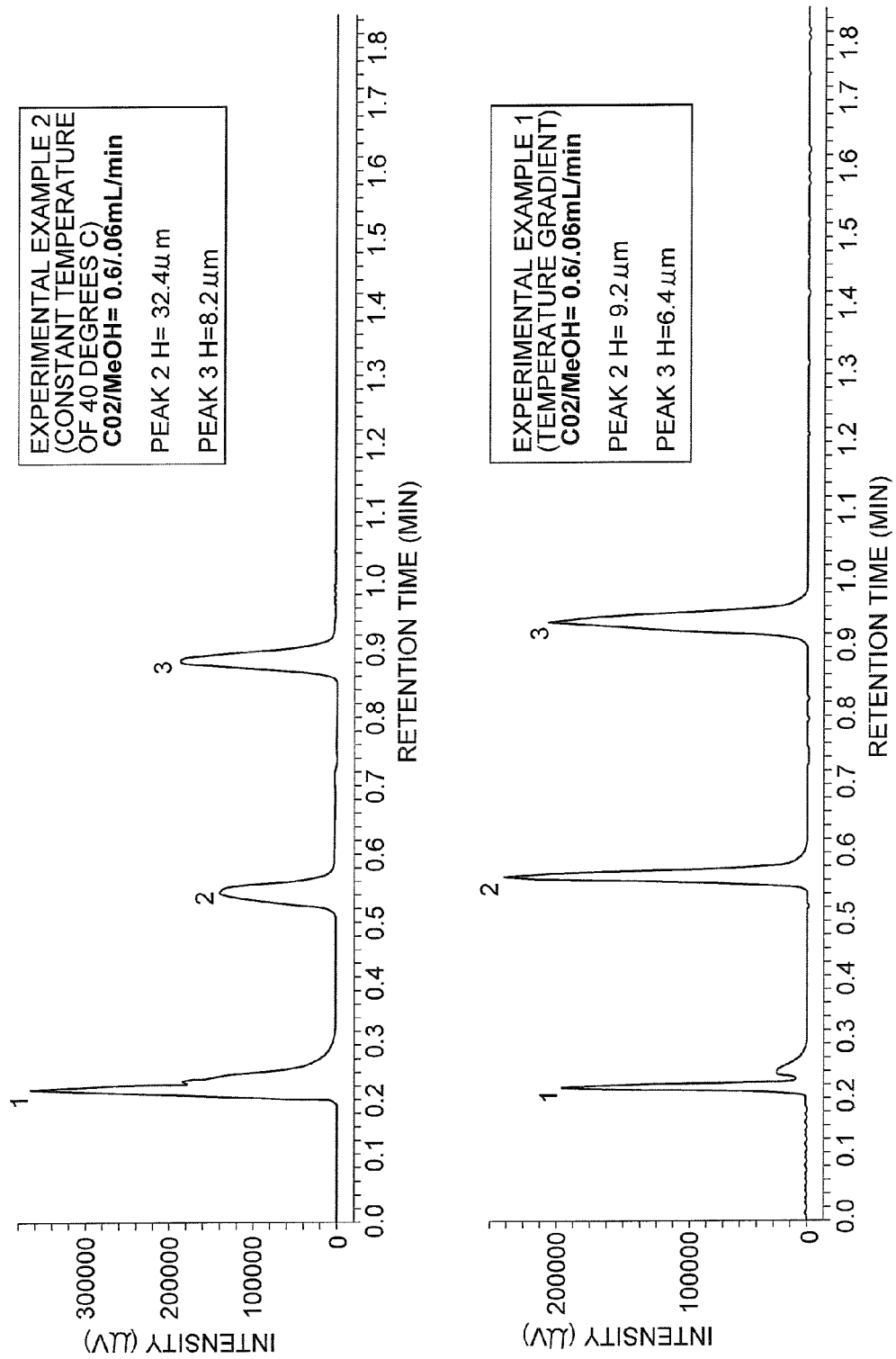
FIG. 22 shows measurement results in the form of chromatogram in Example 2 and Comparative Example 2.

FIG. 22 shows a chromatogram obtained in Experimental Example 1, in which the flow rates of the carbon dioxide/methanol from the pumps were 0.6/0.06 ml/min in the experiment described above. In FIG. 22, the peak 1 represents toluene, the peak 2 represents m-nitroaniline, and the peak 3 represents caffeine.

As Experimental Example 2, the experiment described above was carried out in the following conditions: The preheating coil 210 shown in FIG. 18 was set at 40° C. The temperature control members 220 were not used but the column was placed in a column oven set at 40° C. The temperature in the column was maintained at a fixed value (40° C.). FIG. 22 shows the resultant chromatogram.

FIG. 22 clearly shows that using SFC in which the temperature control member that provides the column with a temperature gradient is disposed not only achieves high resolution, that is, the height equivalent to a theoretical plate of the "peak 2" changing from 32.4 to 9.2 µm and the height equivalent to a theoretical plate of "peak 3" changing from 8.2 to 6.4 µm, but also improves the shape of the peaks in the chromatogram.

Reference Example 2

The apparatus shown in FIG. 19, in which the pressure control apparatus according to the present invention including the valve-opening ratio adjustment member was employed. was used to carry out chromatogram measurement. The bypass channel section 330 was formed by providing T joints upstream and downstream of the injector 308 and connecting them with pipes. The carbon dioxide pump 322 was set to have a carbon dioxide flow rate of 45 ml/min, and the modifier pump 328 was set to have a supplemental solvent (methanol) flow rate of 5 ml/min. The bypass was disposed in such a way that the mobile phase having the composition ratio described above was equally distributed to and flows through the injector 308 and the bypass channel section 330. The injector 308 then injected 1000 µL of sample solution while the mobile phase fluid was delivered in the above condition.

The sample solution was 1.5 mg of ethyl p-hydroxybenzoate in 1 ml of methanol. The column 312 was a packed column having an inner diameter of 20 mm and a length of 250 mm. Silica was used as the microbead which is packed in the column.

Figure 23:
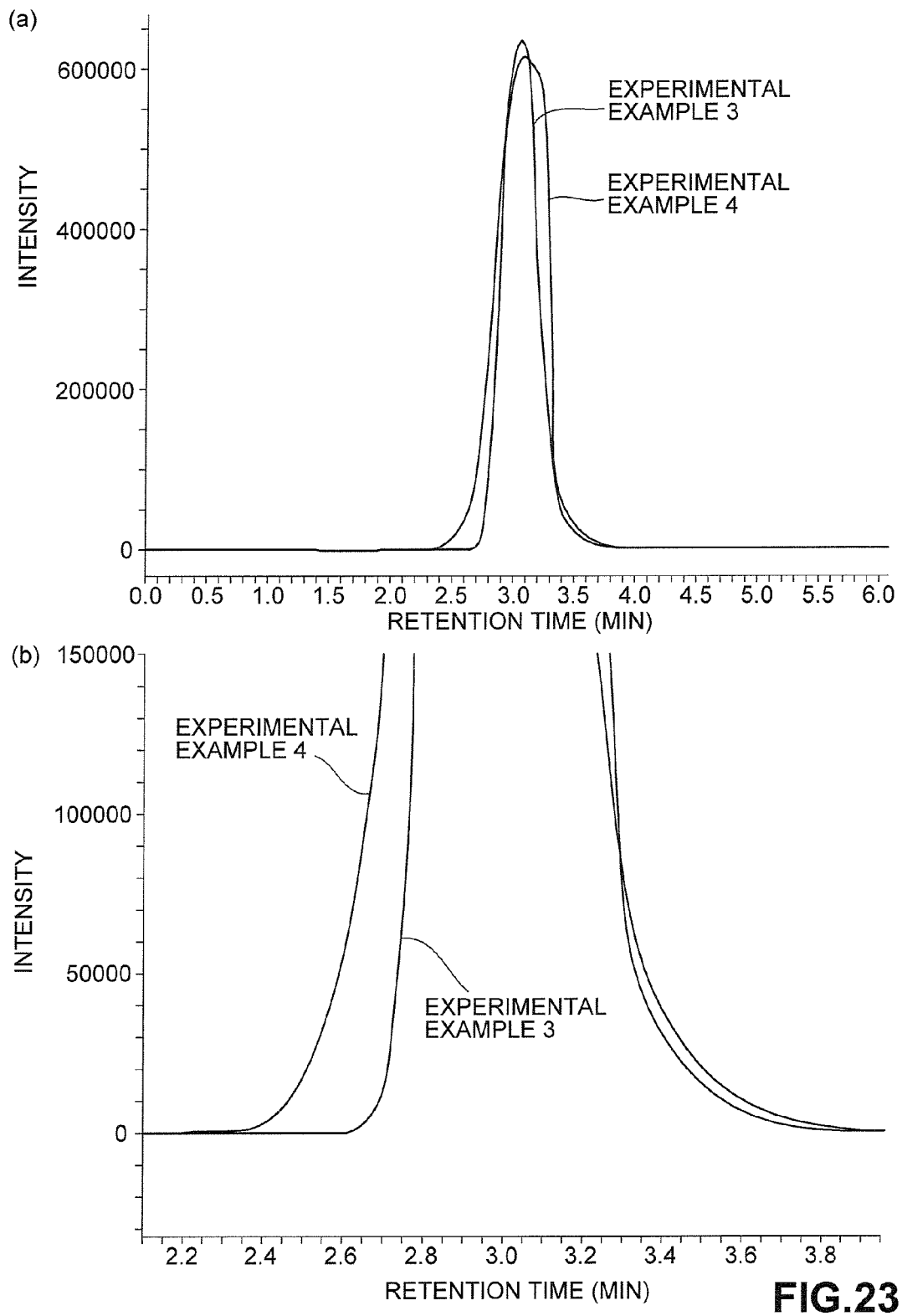
FIGS. 23(A) and 23(B) show measurement results in the form of chromatogram in Example 3 and Comparative Example 3.

FIGS. 23(A) and 23(B) show Experimental Example 3 in which an apparatus including the bypass channel section 330 described above was used to measure a chromatogram and Experimental Example 4 in which an apparatus including no bypass channel section 330 was used to measure a chromatogram, respectively. In Experimental Examples 3 and 4, the apparatus configuration and the measurement conditions were the same except the presence or absence of the bypass channel.

FIG. 23(A) shows graphs obtained by superimposing the measurement results in Experimental Examples 3 and 4. FIG. 23(B) is an enlarged view showing the leading and trailing portions of the peaks in FIG. 23(A).

As shown in FIGS. 23(A) and 23(B), in Experimental Example 3 in which the apparatus including the bypass channel was used, the period from the leading portion to the trailing portion of the peak was shorter by approximately 22% from 1.6 to 1.25 minutes than in Experimental Example 4 in which the apparatus including no bypass was used.

Therefore, using SFC in which a sample injection section including a bypass channel is disposed allows a leading portion to be suppressed in an easy and inexpensive manner. It is therefore obvious that measurement precision and resolution are improved. Further, when a fraction of the peak is recovered, a denser sample can be obtained in a short period.

What is claimed is:

1. A pressure control apparatus for a supercritical fluid comprising:
    (a) a valve comprising:
        (1) a valve chamber provided in a midway portion of a channel through which a supercritical fluid passes, and
        (2) an electrically-operated valve element located in the valve chamber,
    wherein the valve element is configured to be lifted to open the valve and lowered to close the valve, and wherein a front end of the valve element fits into the valve chamber when the valve is closed, and the valve element travels backward when the valve is opened;
    (b) a pressure detection member configured to detect pressure of the supercritical fluid in the channel on an upstream or downstream side of the valve chamber;
    (c) an open/close control member for controlling the pressure detected by the pressure detection member to be a target pressure; and
    (d) a valve-opening ratio adjustment member for automatically adjusting valve-opening ratio when the valve is opened based on state of the supercritical fluid,
    wherein the valve-opening ratio adjustment member includes
    (e) a backward travel restricting section that restricts the valve element from traveling backward to limit a backward travel distance of the valve element when the valve is opened, and
    (f) a backward travel specifying section that specifies an optimum valve-opening ratio and instructs the backward travel restricting section of the specified optimum valve-opening ratio, and
    wherein the open/close control member controls an open/close cycle of the valve in such a way that a period during which the valve element is lifted increases when the detected pressure is higher than the target pressure, and a period during which the valve element is lowered increases when the detected pressure is lower than the target pressure to achieve a target pressure, and the valve-opening ratio adjustment member adjusts the valve-opening ratio when the valve is opened during the open/close cycle, to allow the pressure to be controlled in such a way that the pressure varies within a range that cannot be achieved by only controlling the valve open/close cycle;
    the pressure control apparatus controls the pressure of the supercritical fluid to the target pressure by the open/close cycle and the valve-opening ratio when the valve is opened during the open/close cycle; and
    the valve element is configured to be lifted and lowered in the valve chamber during the open/close cycle at a frequency within a range of from more than 2 Hz to 100 Hz.

2. The pressure control apparatus for a supercritical fluid according to claim 1,
wherein the valve-opening ratio adjustment member includes a piezoelectric actuator, and
the piezoelectric actuator expands or contracts to adjust the backward travel of the valve element when the valve is opened.

3. The pressure control apparatus for a supercritical fluid according to claim 1,
wherein the valve-opening ratio adjustment member includes a table representing the relationship between an optimum gap length when the valve is opened and composition of the supercritical fluid.

4. The pressure control apparatus for a supercritical fluid according to claim 1,
wherein when the detected pressure deviates from the target pressure, the valve-opening ratio adjustment member automatically adjusts a gap length to an optimum value so as to minimize the difference between the detected pressure and the target pressure.

5. The pressure control apparatus for a supercritical fluid according to claim 1,
wherein the valve-opening ratio adjustment member monitors variation in the detected pressure and automatically adjusts a gap length to an optimum value so as to minimize the variation.

6. The pressure control apparatus for a supercritical fluid according to claim 2,
wherein the valve-opening ratio adjustment member includes a table representing the relationship between an optimum gap length when the valve is opened and composition of the supercritical fluid.

7. The pressure control apparatus for a supercritical fluid according to claim 2,
wherein when the detected pressure deviates from the target pressure, the valve-opening ratio adjustment member automatically adjusts a gap length to an optimum value so as to minimize the difference between the detected pressure and the target pressure.

8. The pressure control apparatus for a supercritical fluid according to claim 2,
wherein the valve-opening ratio adjustment member monitors variation in the detected pressure and automatically adjusts a gap length to an optimum value so as to minimize the variation.

9. The pressure control apparatus for a supercritical fluid according to claim 1, further comprising a flow rate sensor configured to detect a flow rate of the supercritical fluid.

10. The pressure control apparatus for a supercritical fluid according to claim 1,
wherein the valve-opening ratio adjustment member includes a table representing the relationship between an optimum gap length when the valve is opened and a pressure of the supercritical fluid.

11. The pressure control apparatus for a supercritical fluid according to claim 1,
wherein the valve-opening ratio adjustment member includes a table representing the relationship between an optimum gap length when the valve is opened and a flow rate of the supercritical fluid.

12. A supercritical fluid chromatography apparatus comprising a pressure control apparatus of claim 1 and a pump, wherein based on values programmed in the pump given in advance to the pressure control apparatus, the pressure control apparatus adjusts the valve-opening ratio at the same time when settings of the pump are changed.

* * * * *